US009421532B2

(12) United States Patent
Nagashima et al.

(10) Patent No.: US 9,421,532 B2
(45) Date of Patent: Aug. 23, 2016

(54) MONONUCLEAR IRON COMPLEX AND ORGANIC SYNTHESIS REACTION USING SAME

(71) Applicants: KYUSHU UNIVERSITY, NATIONAL UNIVERSITY CORPORATION, Fukuoka-shi, Fukuoka (JP); SHIN-ETSU CHEMICAL CO., LTD., Tokyo (JP)

(72) Inventors: Hideo Nagashima, Kasuga (JP); Yusuke Sunada, Kasuga (JP); Hironori Tsutsumi, Kasuga (JP); Toru Hashimoto, Kasuga (JP); Koji Sakuta, Annaka (JP)

(73) Assignees: KYUSHU UNIVERSITY, NATIONAL UNIVERSITY CORPORATION, Fukuoka-Shi (JP); SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/771,757

(22) PCT Filed: Feb. 26, 2014

(86) PCT No.: PCT/JP2014/054718
§ 371 (c)(1),
(2) Date: Aug. 31, 2015

(87) PCT Pub. No.: WO2014/133017
PCT Pub. Date: Sep. 4, 2014

(65) Prior Publication Data
US 2016/0023196 A1    Jan. 28, 2016

(30) Foreign Application Priority Data

Mar. 1, 2013    (JP) .................................. 2013-040874

(51) Int. Cl.
| | | |
|---|---|---|
| *B01J 31/16* | (2006.01) | |
| *C07F 15/02* | (2006.01) | |
| *C07D 223/04* | (2006.01) | |
| *C07C 5/03* | (2006.01) | |
| *C07C 29/147* | (2006.01) | |
| *C07C 41/26* | (2006.01) | |

(Continued)

(52) U.S. Cl.
CPC .............. *B01J 31/1608* (2013.01); *B01J 31/20* (2013.01); *B01J 31/226* (2013.01); *C07C 5/03* (2013.01); *C07C 29/14* (2013.01); *C07C 29/147* (2013.01); *C07C 41/18* (2013.01); *C07C 41/26* (2013.01); *C07C 209/50* (2013.01); *C07C 213/00* (2013.01); *C07C 213/02* (2013.01); *C07C 227/06* (2013.01); *C07C 227/16* (2013.01); *C07C 227/18* (2013.01); *C07D 223/04* (2013.01); *C07F 7/0809* (2013.01); *C07F 7/0829* (2013.01); *C07F 15/02* (2013.01); *B01J 2231/323* (2013.01); *B01J 2231/643* (2013.01); *B01J 2231/645* (2013.01); *B01J 2531/842* (2013.01); *C07C 2101/08* (2013.01); *C07C 2101/14* (2013.01); *C07C 2531/16* (2013.01); *C07C 2531/20* (2013.01); *C07C 2531/22* (2013.01); *Y02P 20/52* (2015.11)

(58) Field of Classification Search
CPC .... B01J 31/1608; C07F 15/02; C07D 223/04; C07C 5/03; C07C 29/14; C07C 41/18; C07C 209/50; C07C 213/00; C07C 227/06
USPC ............. 540/484; 556/12; 564/385; 568/650, 568/715, 813, 830; 585/268, 270, 276
See application file for complete search history.

(56) References Cited

FOREIGN PATENT DOCUMENTS

| | | |
|---|---|---|
| JP | 2011-45798 A | 3/2011 |
| WO | WO 96/05207 A1 | 2/1996 |

OTHER PUBLICATIONS

English machine language translation of JP 2011-045798 (Dec. 13, 2015).*

(Continued)

*Primary Examiner* — Porfirio Nazario Gonzalez
(74) *Attorney, Agent, or Firm* — Birch, Stewart, Kolasch & Birch, LLP

(57) ABSTRACT

Provided is a mononuclear iron complex that comprises an iron-silicon bond that is represented by formula (1) and that exhibits excellent catalyst activity in each of a hydrosilylation reaction, a hydrogenation reaction, and reduction of a carbonyl compound.

(1)

$$\begin{array}{c} R^2 \phantom{x} R^1 \\ R^3 - Si \\ \phantom{xxx} \diagdown \\ \phantom{xxxxx} Fe(CO)_n L_m \\ \phantom{xxx} \diagup \\ R^4 - Si \\ R^5 \phantom{x} R^6 \end{array}$$

In formula (1), $R^1$-$R^6$ either independently represent an alkyl group, an aryl group, an aralkyl group or the like that may be substituted with a hydrogen atom or X, or represent a crosslinking substituent in which at least one pair comprising one of $R^1$-$R^3$ and one of $R^4$-$R^6$ is combined. X represents a halogen atom, an organoxy group, or the like. L represents a two-electron ligand other than CO. When a plurality of L are present, the plurality of L may be the same as or different from each other. When two L are present, the two L may be bonded to each other. n and m independently represent an integer of 1 to 3 with the stipulation that n+m equals 3 or 4.

15 Claims, 2 Drawing Sheets

(51) Int. Cl.
| | |
|---|---|
| C07C 209/50 | (2006.01) |
| B01J 31/20 | (2006.01) |
| B01J 31/22 | (2006.01) |
| C07C 213/02 | (2006.01) |
| C07C 227/16 | (2006.01) |
| C07C 227/18 | (2006.01) |
| C07C 29/14 | (2006.01) |
| C07F 7/08 | (2006.01) |
| C07C 41/18 | (2006.01) |
| C07C 213/00 | (2006.01) |
| C07C 227/06 | (2006.01) |

(56) References Cited

OTHER PUBLICATIONS

Bart et al. "Preparation and Molecular and Electronic Structures of Iron(0) Dinitrogen and Silane Complexes and Their Application to Catalytic Hydrogenation and Hydrosilation", Journal of the American Chemical Society, 2004, vol. 126, No. 42, pp. 13794-13807.
Brown et al., "Reductions by Lithium Aluminum Hydride", Organic Reactions, 1941, Chapter 10, 6, pp. 469-493.
Carre et al., "Reactivity of μ-silanediyl iron carbonyl complexes with alkynes", Inorganic Chemistry, American Chemical Society, 1982, vol. 21, No. 8, pp. 3099-3105.
Daida et al., "Considering FeII/IV Redox Processes as Mechanistically Relevant to the Catalytic Hydrogenation of Olefins by [PhBPiPr3]Fe-Hx Species", Inorganic Chemistry, 2004, vol. 43, No. 23, pp. 7474-7485.
Das et al., "Two Iron Catalysts are Better than One: A General and Convenient Reduction of Aromatic and Aliphatic Primary Amides", Angew. Chem. Int. Ed. 2012, 51, pp. 1662-1666.
Frankel et al., "Homogeneous Hydrogenation of Methyl Linoleate Catalyzed by Iron Pentacarhonyl. Characterization of Methyl Octadecadienoate-Iron Tricarhonyl Complexes1", J. Org. Chem., 1964, vol. 29, pp. 3292-3297.
Harmon et al., "Hydrogenation of Organic Compounds Using Homogeneous Catalysts", Chemical Reviews, 1973, vol. 73, No. 1, pp. 21-52.
Heyn et al., "Coordinatively and electronically unsaturated tris(trimethylsilyl)silyl complexes of manganese and iron", Inorganica Chimica Acta, 2002, vol. 341, pp. 91-98.
Inagaki et al., "Asymmetric Iron-Catalyzed Hydrosilane Reduction of Ketones: Effect of Zinc Metal upon the Absolute Configuration", Angew. Chem. Int. Ed. 2010, 49, 9384-9387.
Inagaki et al., "Iron- and Cobalt-Catalyzed Asymmetric Hydrosilylation of Ketones and Enones with Bis(oxazolinylphenyl)amine Ligands", Chem. Eur. J. 2010, 16, 3090-3096.
International Search Report issued in PCT/JP2014/054718, mailed on Apr. 28, 2014.
Kamata et al., "Catalytic Hydrosilylation of Alkenes by Iron Complexes Containing Terpyridine Derivatives as Ancillary Ligands", Organometallics, American Chemical Society, 2012, 31, 3825-3828.

Lee et al., "From Tetragermacyclobutene to Tetragermacyclobutadiene Dianion to Tetragermacyclobutadiene Transition Metal Complexes", Journal of the American Chemical Society 2011, vol. 133, pp. 5103-5108.
Naumov et al., "Selective Dehydrogenative Silylation-Hydrogenation Reaction of Divinyldisiloxane with Hydrosilane Catalyzed by an Iron Complex", Journal of the American Chemical Society, 2012, 134, 804-807.
Nesmeyanov et al., "Addition, Substitution, and Telomerization Reactions of Olefins in the Presence of Metal Carbonyls or Colloidal Iron", Tetrahedron, 1962, vol. 17, pp. 61-68.
Rangheard et al., "At the frontier between heterogeneous and homogeneous catalysis: hydrogenation of olefins and alkynes with soluble iron nanoparticles", The Royal Society of Chemistry, Dalton Transactions, 2010, 39, 8464-8471.
Sakurai et al., "n3-1-Silapropenyltricarbonyliron complexes,The First Stable Compound of Doubly Bonded Sillcon1", Journal of the American Chemical Society, Nov. 10, 1976, vol. 98, pp. 7453-7454.
Sato et al., "Alkoxyhydrosilanes as sources of silylene ligands: Novel approaches to transition metal-silylene complexes", Chemistry Letters, The Chemical Society of Japan, 2004, vol. 33, No. 7, pp. 868-869.
Schroeder et al., "Pentacarbonyliron(O) Photocatalyzed Hydrogenation and Isomerization of Olefins", Journal of the American Chemical Society, Jan. 21, 1976, 98:2, pp. 551-558.
Schroeder et al., "Pentacarbonyliron(O) Photocatalyzed Reactions of Trialkylsilanes With Alkenes", Journal of Organometallic Chemistry, 1977, 128, pp. 345-358.
Schubert et al., "Investigations on the reactivity of the anionic silyl complexes [Fe(CO) 3 (PR3') SiR3]-", Chemische Berichte, 1987, vol. 120, pp. 1079-1085.
Sunada et al., "Catalyst design for iron-promoted reductions: an iron disilyl-dicarbonyl complex bearing weakly coordinating n2—(H—Si) moieties", The Royal Society of Chemistry, Dalton Transactions, 2013, vol. 42, pp. 16687-16692.
Sunada et al., "Hydrosilane Reduction of Tertiary Carboxamides by Iron Carbonyl Catalysts", Angew. Chem. Int. Ed. 2009, 48, pp. 9511-9514.
Takanashi et al., "A (tetrasilacyclobutadiene) tricarbonyliron complex[ {n4-(tBu2MeSi) 4Si4 } Fe(C0)3]: the silicon cousin of Pettit's (cyclobutadiene)tricarbonyliron complex [ (n4-H4C4)Fe(C0)3]", Angewandte Chemie, International Edition, 2006, vol. 45, pp. 3269-3272.
Tondreau et al., "Iron Catalysts for Selective Anti-Markovnikov Alkene Hydrosilylation Using Tertiary Silanes", Science, Feb. 3, 2012, vol. 335, pp. 567-570.
Tsutsumi et al., "New catalyst systems for iron-catalyzed hydrosilane reduction of carboxamides", The Royal Society of Chemistry, Chem. Commun., 2011, 47, pp. 6581-6583.
Written Opinion issued in PCT/JP2014/054718, mailed on Apr. 28, 2014.
Zhou et al., "A Convenient and General Iron-Catalyzed Reduction of Amides to Amines", Angew. Chem. Int. Ed. 2009, 48, pp. 9507-9510.

* cited by examiner

MONONUCLEAR IRON COMPLEX AND ORGANIC SYNTHESIS REACTION USING SAME

TECHNICAL FIELD

This invention relates to a mononuclear iron complex having iron-silicon bonds, and more particularly, to a mononuclear iron complex having catalytic activity to three reactions: hydrosilylation reaction, hydrogenation reaction, and reductive reaction of carbonyl compounds.

BACKGROUND ART

Hydrosilylation reaction involving addition reaction of a Si—H functionality compound to a compound having a carbon-carbon double or triple bond is a useful means for synthesizing organosilicon compounds and is also industrially important synthetic reaction.

Pt, Pd and Rh compounds are known as catalysts for the hydrosilylation reaction. Most often used among them are Pt compounds as typified by Speier catalysts and Karstedt catalysts.

One of problems associated with Pt compound-catalyzed reactions is that the addition of a Si—H functionality compound to terminal olefin entails side reaction or internal rearrangement of olefin. Since this system does not display addition reactivity to internal olefin, unreacted olefin is left in the addition product. To complete the reaction, the olefin must be used previously in excess by taking into account the portion that is left behind due to side reaction.

Another problem is low selectivity between $\alpha$- and $\beta$-adducts depending on the identity of olefin.

The most serious problem is that all Pt, Pd and Rh as the center metal are very expensive noble metal elements. Since metal compound catalysts which can be used at lower cost are desired, a number of research works have been made thereon.

For example, reaction in the presence of iron-carbonyl complexes such as $Fe(CO)_5$ and $Fe_3(CO)_{12}$ is known from Non-Patent Document 1. For this reaction, reaction conditions including a high temperature of 160° C., or light irradiation is necessary (Non-Patent Document 2).

Non-Patent Document 3 reports exemplary reaction of methylvinyldisiloxane with methylhydrogendisiloxane using an iron-carbonyl complex having a cyclopentadienyl group as ligand. In this reaction, dehydrogenation silylation reaction takes place preferentially.

Non-Patent Document 4 describes reaction using an iron catalyst having a pyridine ligand. A large excess of reducing agent ($NaBHEt_3$) is necessary as reaction aid. Although $PhSiH_3$ and $Ph_2SiH_2$ add to olefins, more useful trialkylsilanes, alkoxysilanes and siloxanes have poor addition reactivity to olefins.

Non-Patent Documents 5 and 6 report Fe complexes having a bisiminopyridine ligand. It is disclosed that they display good reactivity to alkoxysilanes and siloxanes under mild conditions. The reaction using these complexes, however, has several problems including low reactivity to internal olefin, use of sodium amalgam, which consists of water-prohibitive sodium and highly toxic mercury and requires careful handling, or use of water-prohibitive $NaBEt_3H$ during the synthesis of the complex, and low stability of the complex compound itself, which requires handling in a special equipment like glovebox and storage in nitrogen atmosphere.

On the other hand, a number of reports are made on hydrogenation reaction of olefins. For example, Non-Patent Document 7 reports hydrogenation by thermal reaction using $Fe(CO)_5$ catalyst, and Non-Patent Document 8 reports hydrogenation by photo-reaction. However, the thermal reaction requires high-temperature (180° C.) and high-pressure (28 atm.) conditions, and the turnover count is as low as 0.5. It is not concluded that the catalyst has sufficient activity. Also the photo-reaction can take place even at room temperature, but a turnover count of 33 is still insufficient.

Non-Patent Document 9 reports exemplary reaction using an organoaluminum compound as reaction aid and an iron catalyst. A turnover count of 17 indicates low catalytic activity.

Non-Patent Document 10 reports exemplary reaction using a Grignard compound in combination with an iron chloride catalyst. The system allows reaction to run at room temperature, but requires high-pressure (20 atm.) conditions, and the turnover count is as low as 20.

Non-Patent Document 11 reports an iron catalyst having a phosphorus base compound as ligand. Although the system allows reaction to run at room temperature and a relatively low pressure (4 atm.), the reactants are limited to styrene and some alkenes, and the turnover count is not regarded sufficient.

Also, Non-Patent Document 5 cited above reports an exemplary iron catalyst having a bisiminopyridine ligand. Reactivity is satisfactory as demonstrated by a turnover count of 1,814 at room temperature and a relatively low pressure (4 atm.). This reaction suffers from problems including safety upon synthesis and stability of the relevant compound like the aforementioned iron complex having a bisiminopyridine ligand.

One known method for reducing carbonyl compounds is by using hydrogen in the presence of aluminum hydride, boron hydride or noble metal catalysts. For ketones and aldehydes among carbonyl compounds, there are known hydride promoters and hydrogenation noble metal catalysts which allow progress of reaction under mild conditions and are stable and easy to handle. For reducing carboxylic acid derivatives such as esters and amides, the main method uses strong reducing agents such as lithium aluminum hydride and borane (Non-Patent Document 12). However, since these reducing agents are flammable, water-prohibitive substances, they are awkward to handle. Also careful operation is necessary when the aluminum or boron compound is removed from the desired compound at the end of reaction. In addition, high-temperature/high-pressure hydrogen is necessary for the reduction of carboxylic acid derivatives.

There are reported many methods using methylhydrogenpolysiloxane or hydrosilane compound which is stable in air and easy to handle, as the reducing agent. For this reaction, addition of strong acids or Lewis acids is necessary as well as expensive noble metal catalysts. One recent report relates to reductive reaction of carbonyl compounds in the presence of low cost iron catalysts. In some examples, the catalyst is applied to reductive reaction of amides which requires rigorous conditions in the prior art. While illustrative examples of the iron catalyst are given in Non-Patent Documents 13 to 18, there is a desire to have high activity catalysts displaying a greater turnover count.

Also, examples of the iron complex compound having catalytic activity to three reactions: hydrosilylation reaction, hydrogenation reaction, and reductive reaction of carbonyl compounds, which have been reported heretofore, are only bisiminopyridine complexes by Chirik et al. (Non-Patent Documents 5, 6) and $Fe(CO)_5$. On use of the complexes by Chirik et al., carbonyl compounds of ketone and aldehyde type can be reduced, but reduction of carboxylic acid derivatives is not achievable. On use of $Fe(CO)_5$, reduction of amides as carboxylic acid derivatives with silanes is achievable, but requires a high temperature of at least 100° C. or light irradiation, and a long reaction time (9 to 24 hours), suggesting that reaction under mild conditions is difficult.

CITATION LIST

Non-Patent Documents

Non-Patent Document 1: A. N. Nesmeyanov, et al., *Tetrahedron*, 1962, 17, 61
Non-Patent Document 2: M. A. Schroeder, et al., *J. Organomet. Chem.*, 1977, 128, 345
Non-Patent Document 3: R. N. Naumov, et al., *J. Am. Chem. Soc.*, 2012, 134, 804
Non-Patent Document 4: K. Kamata, et al., *Organometallics*, 2012, 31, 3825
Non-Patent Document 5: S. C. Bart, et al., *J. Am. Chem. Soc.*, 2004, 126, 13794
Non-Patent Document 6: A. N. Tondreau, et al., *Science*, 2012, 335, 567
Non-Patent Document 7: E. N. Frankel, et al., *J. Org. Chem.*, 1964, 29, 3292
Non-Patent Document 8: M. A. Schroeder, et al., *J. Am. Chem. Soc.*, 1976, 98, 551
Non-Patent Document 9: R. E. Harmon, et al., *Chemical Reviews*, 1973, 73, 21
Non-Patent Document 10: C. Rangheard, et al., *Dalton Trans.*, 2010, 39, 8464
Non-Patent Document 11: E. J. Daida, et al., *Inorg. Chem.*, 2004, 43, 7474
Non-Patent Document 12: W. G. Brown, "Reductions by Lithium Aluminum Hydride," Organic Reactions, 1941, Chapter 10, 6, pages 469-493
Non-Patent Document 13: Y. Sunada, et al., *Angew. Chem. Int. Ed.*, 2009, 48, 9511
Non-Patent Document 14: S. Zhou, et al., *Angew. Chem. Int. Ed.*, 2009, 48, 9507
Non-Patent Document 15: Inagaki, et al., *Angew. Chem. Int. Ed.*, 2010, 49, 9384
Non-Patent Document 16: Inagaki, et al., *Chem. Eur. J.*, 2010, 16, 3090
Non-Patent Document 17: Tsutsumi, et al., *Chem. Commun.*, 2011, 47, 6581
Non-Patent Document 18: S. Das, et al., *Angew. Chem. Int. Ed.*, 2012, 51, 1662

SUMMARY OF INVENTION

Technical Problem

An object of the invention, which has been made under the above circumstances, is to provide a mononuclear iron complex having iron-silicon bonds that displays high catalytic activity to three reactions: hydrosilylation reaction, hydrogenation reaction, and reductive reaction of carbonyl compounds, and methods for carrying out hydrosilylation reaction, hydrogenation reaction, and reductive reaction of carbonyl compounds under mild conditions in the presence of the complex.

Solution to Problem

Making extensive investigations to solve the outstanding problems, the inventors have found that a specific mononuclear iron complex having iron-silicon bonds displays high catalytic activity to three reactions: hydrosilylation reaction, hydrogenation reaction, and reductive reaction of carbonyl compounds, and allows hydrosilylation reaction, hydrogenation reaction, and reductive reaction of carbonyl compounds to run under mild conditions. The invention is completed based on this finding.

Namely, the present invention provides the following.

[1] A mononuclear iron complex having formula (1):

[Chemical Formula 1]

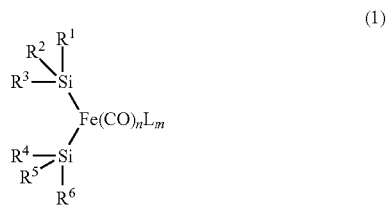

wherein $R^1$ to $R^6$ are each independently hydrogen, or an alkyl, aryl, aralkyl, organoxy, monoorganoamino, diorganoamino, monoorganophosphino, diorganophosphino, monoorganosilyl, diorganosilyl, triorganosilyl or organothio group which may be substituted with X, or at least one pair of any one of $R^1$ to $R^3$ and any one of $R^4$ to $R^6$, taken together, represent a crosslinking substituent; X is a halogen atom, organoxy, monoorganoamino, diorganoamino or organothio group; L is a two-electron ligand other than CO, with the proviso that when a plurality of L's are present, they may be the same or different, and when two L's are present, they may bond together; n and m are each independently an integer of 1 to 3, and n+m is 3 or 4.

[2] The mononuclear iron complex of [1] wherein L is at least one two-electron ligand selected from the group consisting of molecular hydrogen, amine, imine, nitrogen-containing heterocycle, phosphine, arsine, alcohol, thiol, ether, sulfide, nitrile, isonitrile, aldehyde, ketone, $C_2$-$C_{30}$ alkene, $C_2$-$C_{30}$ alkyne, and triorganohydrosilane.

[3] The mononuclear iron complex of [1] or [2] wherein n and m each are 2, and L is at least one ligand selected from sulfide, thiol, and triorganohydrosilane, with the proviso that two L's may bond together.

[4] The mononuclear iron complex of [3] wherein $R^1$ to $R^6$ are each independently an alkyl, aryl or aralkyl group which may be substituted with X which is as defined above, L's are triorganohydrosilanes represented by H—$SiR^7R^8R^9$ and H—$SiR^{10}R^{11}R^{12}$ wherein $R^7$ to $R^{12}$ are each independently an alkyl, aryl or aralkyl group which may be substituted with X which is as defined above, at least one pair of any one of $R^1$ to $R^3$ and any one of $R^4$ to $R^6$ or any one of $R^7$ to $R^9$, or at least one pair of any one of $R^{10}$ to $R^{12}$ and any one of $R^4$ to $R^6$ or any one of $R^7$ to $R^9$ may bond together to form a crosslinking substituent, or at least one pair of any one of $R^1$ to $R^3$ and any one of $R^4$ to $R^6$ or any one of $R^7$ to $R^9$ may bond together to form a crosslinking substituent, and at least one pair of any one of $R^{10}$ to $R^{12}$ and any one of $R^4$ to $R^6$ or any one of $R^7$ to $R^9$ may bond together to form a crosslinking substituent.

[5] The mononuclear iron complex of [3] wherein $R^1$ to $R^6$ are each independently an alkyl, aryl or aralkyl group which may be substituted with X which is as defined above, L's are sulfides or thiols represented by $SR^{13}R^{14}$ and $SR^{15}R^{16}$ wherein $R^{13}$ to $R^{16}$ are each independently hydrogen or an alkyl, aryl or aralkyl group which may be substituted with X which is as defined above, at least one pair of either one of $R^{13}$ and $R^{14}$ and either one of $R^{15}$ and $R^{16}$ may bond together to form a crosslinking substituent.

[6] The mononuclear iron complex of any one of [1] to [5] wherein a pair of any one of $R^1$ to $R^3$ and any one of $R^4$ to $R^6$ bond together to form a crosslinking substituent.

[7] The mononuclear iron complex of [4] wherein any one of $R^1$ to $R^3$ and any one of $R^4$ to $R^6$ or any one of $R^7$ to $R^9$ bond together to form a crosslinking substituent, and any one of $R^{10}$ to $R^{12}$ and a substituent on Si which is selected from any one of $R^4$ to $R^6$ and any one of $R^7$ to $R^9$ and which does not participate in formation of said crosslinking substituent, bond together to form a crosslinking substituent.

[8] The mononuclear iron complex of [5] or [6] wherein either one of $R^{13}$ and $R^{14}$ and either one of $R^{15}$ and $R^{16}$ bond together to form a crosslinking substituent.

[9] The mononuclear iron complex of [7] wherein any one of $R^1$ to $R^3$ and any one of $R^4$ to $R^6$ bond together to form an o-phenylene group which may be substituted with Y, Y is hydrogen, halogen, $C_1$-$C_{10}$ alkyl, or $C_1$-$C_{10}$ alkoxy group, with the proviso that when a plurality of Y's are present, they may be the same or different, and any one of $R^{10}$ to $R^{12}$ and any one of $R^7$ to $R^9$ bond together to form an o-phenylene group which may be substituted with Y which is as defined above.

[10] The mononuclear iron complex of [8] wherein any one of $R^1$ to $R^3$ and any one of $R^4$ to $R^6$ bond together to form an o-phenylene group which may be substituted with Y, Y is hydrogen, halogen, $C_1$-$C_{10}$ alkyl, or $C_1$-$C_{10}$ alkoxy group, with the proviso that when a plurality of Y's are present, they may be the same or different, and either one of $R^{13}$ and $R^{14}$ and either one of $R^{15}$ and $R^{16}$ bond together to form a $C_1$-$C_6$ alkylene group.

[11] A catalyst comprising the mononuclear iron complex of any one of [1] to [10], the catalyst having activity to three reactions: hydrosilylation reaction, hydrogenation reaction, and reductive reaction of carbonyl compounds.

[12] A method for preparing an addition compound, comprising the step of effecting hydrosilylation reaction of a compound having an aliphatic unsaturated bond with a hydrosilane or organohydropolysiloxane having a Si—H bond in the presence of the catalyst of [11].

[13] A method for preparing an alkane compound, comprising the step of hydrogenating a compound having an aliphatic unsaturated bond in the presence of the catalyst of [11].

[14] A method for preparing an amine compound, comprising the step of reducing an amide compound with a silane or organohydropolysiloxane having a Si—H bond in the presence of the catalyst of [11].

[15] A method for preparing an alcohol compound, comprising the step of reducing an aldehyde, ketone or ester compound with a silane or organohydropolysiloxane having a Si—H bond in the presence of the catalyst of [11].

Advantageous Effects of Invention

When hydrosilylation reaction of an aliphatic unsaturated group-containing compound with a silane or polysiloxane having a Si—H group is carried out using a mononuclear iron complex compound of the invention as the catalyst, addition reaction can occur under conditions from room temperature to 100° C. In particular, addition reaction with industrially useful polysiloxanes, and trialkoxysilanes and dialkoxysilanes takes place in an effective manner. Although the known documents indicate that in the relevant reaction, addition reaction to unsaturated group and dehydrogenation silylation reaction to form unsaturated group-containing compounds often take place concurrently, the use of the inventive catalyst ensures selective progress of addition reaction to unsaturated group. In the reaction with internal olefin, which is difficult with prior art catalysts, an addition reaction product can be formed concomitant with migration of unsaturated group to the terminal.

Hydrogenation reaction is possible under mild conditions including room temperature and atmospheric pressure of hydrogen gas. The catalyst is also effective for hydrogenation of multi-substituted alkenes which is difficult with prior art methods.

In reductive reaction of carbonyl compounds, amide, aldehyde, ketone and ester compounds may be reacted with silanes or polysiloxanes having a Si—H group which are easy to handle, thereby yielding the desired reduced compounds.

Another advantage of the complex compound of the invention is that a common complex compound displays high catalytic activity to a plurality of reactions including hydrosilylation reaction, hydrogenation reaction, and reductive reaction of carbonyl compounds. The complex compound is very useful in organic synthetic reactions.

DESCRIPTION OF EMBODIMENTS

Figure 1:
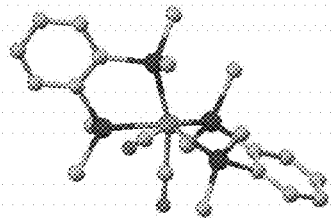
FIG. 1 illustrates the geometry of iron complex A obtained in Example 1.

Now the invention is described in detail.

The invention provides a mononuclear iron complex having Fe—Si bonds and having at least one carbon monoxide (CO) coordinated to Fe, as represented by formula (1).

[Chemical Formula 2]

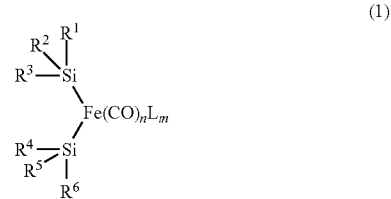

(1)

It is noted that in the mononuclear iron complex of formula (1), when two CO's and two L's are contained (which are distinguishably represented by $L^1$ and $L^2$, respectively), for example, there exist coordination geometry isomers as so depicted by the following formulae. The mononuclear iron complex encompasses all such coordination geometry isomers.

[Chemical Formula 3]

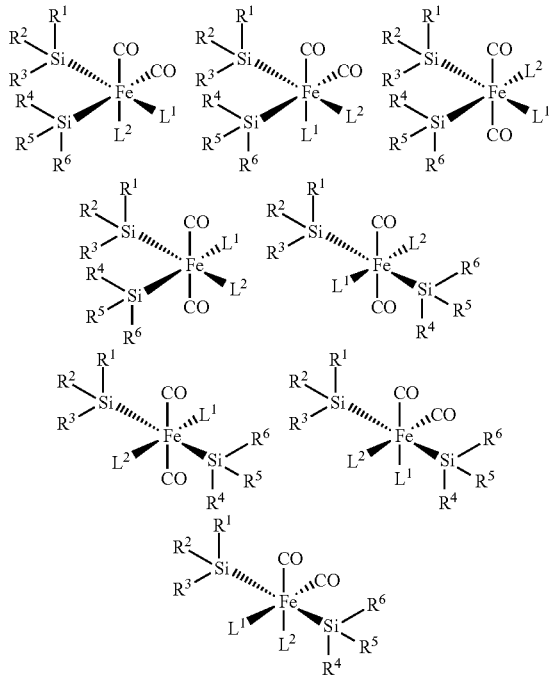

In the mononuclear iron complex of the invention, carbon monoxide (CO) is an essential coordinate moiety to display catalytic activity. While n is an integer of 1 to 3, n is preferably equal to 1 or 2, most preferably 2 for further enhancement of catalytic activity.

$R^1$ to $R^6$ are each independently hydrogen, or an alkyl, aryl, aralkyl, organoxy, monoorganoamino, diorganoamino, monoorganophosphino, diorganophosphino, monoorganosilyl, diorganosilyl, triorganosilyl or organothio group which may be substituted with X, or at least one pair of any one of $R^1$ to $R^3$ and any one of $R^4$ to $R^6$, taken together, represent a crosslinking substituent, and X is a halogen atom, an organoxy, monoorganoamino, diorganoamino or organothio group.

The alkyl group may be straight, branched or cyclic. Although its carbon count is not particularly limited, alkyl groups of 1 to 30 carbons, more preferably 1 to 10 carbons are preferable. Examples include straight or branched alkyl groups such as methyl, ethyl, n-propyl, isopropyl, n-butyl, isobutyl, s-butyl, t-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, and n-eicosanyl; and cycloalkyl groups such as cyclopropyl, cyclobutyl, cyclopentyl, cyclohexyl, cycloheptyl, cyclooctyl, and cyclononyl.

For the aryl group, aryl groups of 6 to 30 carbons, more preferably 6 to 20 carbons are preferable although the carbon count is not particularly limited. Examples include phenyl, 1-naphthyl, 2-naphthyl, anthryl, phenanthryl, o-biphenylyl, m-biphenylyl, and p-biphenylyl.

For the aralkyl group, aralkyl groups of 7 to 30 carbons, more preferably 7 to 20 carbons are preferable although the carbon count is not particularly limited. Examples include benzyl, phenylethyl, phenylpropyl, naphthylmethyl, naphthylethyl, and naphthylpropyl.

Suitable organooxy groups include, but are not limited to, alkoxy, aryloxy and aralkyloxy groups represented by RO wherein R is a substituted or unsubstituted $C_1$-$C_{30}$ alkyl group, $C_6$-$C_{30}$ aryl group or $C_7$-$C_{30}$ aralkyl group.

Suitable alkoxy group include, but are not limited to, alkoxy groups of 1 to 30 carbons, more preferably 1 to 10 carbons are preferable. Examples include methoxy, ethoxy, n-propoxy, i-propoxy, c-propoxy, n-butoxy, i-butoxy, s-butoxy, t-butoxy, n-pentoxy, n-hexoxy, n-heptyloxy, n-octyloxy, n-nonyloxy, and n-decyloxy.

Suitable aryloxy groups include, but are not limited to, aryloxy groups of 6 to 30 carbons, more preferably 6 to 20 carbons are preferable. Examples include phenoxy, 1-naphthyloxy, 2-naphthyloxy, anthryloxy, and phenanthryloxy.

Suitable aralkyloxy groups include, but are not limited to, aralkloxy groups of 7 to 30 carbons, more preferably 7 to 20 carbons are preferable. Examples include benzyloxy, phenylethyloxy, phenylpropyloxy, 1 or 2-naphthylmethyloxy, 1 or 2-naphthylethyloxy, 1 or 2-naphthylpropyloxy.

Suitable organothio groups include the foregoing organoxy groups whose oxygen atom is replaced by sulfur atom.

The monoorganoamino group is preferably a group of $RNH_2$ wherein R is as defined above, though not limited thereto. The preferred carbon count of R is the same as defined above for the alkoxy, aryloxy and aralkyloxy groups. Examples include straight or branched monoalkylamino groups such as methylamino, ethylamino, n-propylamino, isopropylamino, n-butylamino, isobutylamino, s-butylamino, t-butylamino, n-pentylamino, n-hexylamino, n-heptylamino, n-octylamino, n-nonylamino, n-decylamino, n-undecylamino, n-dodecylamino, n-tridecylamino, n-tetradeylamino, n-pentadecylamino, n-hexadecylamino, n-heptadecylamino, n-octadecylamino, n-nonadecylamino, and n-eicosanylamino; monocycloalkylamino groups such as cyclopropylamino, cyclobutylamino, cyclopentylamino, cyclohexylamino, cycloheptylamino, cyclooctylamino, and cyclononylamino; monoarylamino groups such as anilino, 1 or 2-naphthylamino; and monoaralkylamino groups such as benzylamino, phenylethylamino, phenylpropylamino, 1 or 2-naphthylmethylamino.

The diorganoamino group is preferably a group of $R_2NH$ wherein R is independently as defined above, though not limited thereto. The preferred carbon count of R is the same as defined above for the alkoxy, aryloxy and aralkyloxy groups. Examples include straight or branched dialkylamino groups such as dimethylamino, diethylamino, di-n-propylamino, diisopropylamino, di-n-butylamino, diisobutylamino, di-s-butylamino, di-t-butylamino, di-n-pentylamino, di-n-hexylamino, di-n-heptylamino, di-n-octylamino, di-n-nonylamino, di-n-decylamino, di-n-undecylamino, di-n-dodecylamino, di-n-tridecylamino, di-n-tetradeylamino, di-n-pentadecylamino, di-n-hexadecylamino, di-n-heptadecylamino, di-n-octadecylamino, di-n-nonadecylamino, di-n-eicosanylamino, N-ethylmethylamino, N-isopropylmethylamino, and N-butylmethylamino; dicycloalkylamino groups such as dicyclopropylamino, dicyclobutylamino, dicyclopentylamino, dicyclohexylamino, dicycloheptylamino, dicyclooctylamino, dicyclononylamino, and cyclopentylcyclohexylamino; alkylarylamino groups such as N-methylanilino, N-ethylanilino, and N-n-propylanilino; diarylamino groups such as diphenylamino, 4,4'-bisnaphthylamino, N-phenyl-1 or 2-naphthylamino; and diaralkylamino groups such as dibenzylamino, bis(phenylethyl)amino, bis(phenylpropyl)amino, bis(1 or 2-naphthylmethyl)amino.

The monoorganophosphino group is preferably a group of RPH wherein R is independently as defined above, though not limited thereto. The preferred carbon count of R is the same as defined above for the alkoxy, aryloxy and aralkyloxy groups. Examples include straight or branched monoalkylphosphino groups such as methylphosphino, ethylphosphino, n-propylphosphino, isopropylphosphino, n-butylphosphino, isobutylphosphino, s-butylphosphino, t-butylphosphino, n-pentylphosphino, n-hexylphosphino, n-heptylphosphino, n-octylphosphino, n-nonylphosphino, n-decylphosphino, n-undecylphosphino, n-dodecylphosphino, n-tridecylphosphino, n-tetradeylphosphino, n-pentadecylphosphino, n-hexadecylphosphino, n-heptadecylphosphino, n-octadecylphosphino, n-nonadecylphosphino, and n-eicosanylphosphino; monocycloalkylphosphino groups such as cyclopropylphosphino, cyclobutylphosphino, cyclopentylphosphino, cyclohexylphosphino, cycloheptylphosphino, cyclooctylphosphino, and cyclononylphosphino; monoarylphosphino groups such as phenylphosphino, 1 or 2-naphthylphosphino; and monoaralkylphosphino groups such as benzylphosphino.

The diorganophosphino group is preferably a group of $R_2P$ wherein R is independently as defined above, though not limited thereto. The preferred carbon count of R is the same as defined above for the alkoxy, aryloxy and aralkyloxy groups. Examples include straight or branched dialkylphosphino groups such as dimethylphosphino, diethylphosphino, di-n-propylphosphino, diisopropylphosphino, di-n-butylphosphino, diisobutylphosphino, di-s-butylphosphino, di-t-butylphosphino, di-n-pentylphosphino, di-n-hexylphosphino, di-n-heptylphosphino, di-n-octylphosphino, di-n-nonylphosphino, di-n-decylphosphino, di-n-undecylphosphino, di-n-dodecylphosphino, di-n-tridecylphosphino, di-n-tetradeylphosphino, di-n-pentadecylphosphino, di-n-hexadecylphosphino, di-n-heptadecylphosphino, di-n-octadecylphosphino, di-n-nonadecylphosphino, and di-n-eicosanylphosphino; dicycloalkylphosphino groups such as dicyclopropylphosphino, dicyclobutylphosphino, dicyclopentylphosphino, dicyclohexylphosphino, dicycloheptylphosphino, dicyclooctylphosphino, and dicyclononylphosphino; alkylarylphosphino groups such as cyclohexylphenylphosphino; diarylphosphino groups such as diphenylphosphino,
bis(1 or 2-naphthyl)phosphino; and diaralkylphosphino groups such as dibenzylphosphino, bis(phenylethyl)phosphino,
bis(1 or 2-naphthylmethyl)phosphino.

The monoorganosilyl group is preferably a group of $RSiH_2$ wherein R is as defined above, though not limited thereto. The preferred carbon count of R is the same as defined above for the alkoxy, aryloxy and aralkyloxy groups. Examples include straight or branched monoalkylsilyl groups such as methylsilyl, ethylsilyl, n-propylsilyl, isopropylsilyl, n-butylsilyl, isobutylsilyl, s-butylsilyl, t-butylsilyl, n-pentylsilyl, n-hexylsilyl, n-heptylsilyl, n-octylsilyl, n-nonylsilyl, n-decylsilyl, n-undecylsilyl, n-dodecylsilyl, n-tridecylsilyl, n-tetradeylsilyl, n-pentadecylsilyl, n-hexadecylsilyl, n-heptadecylsilyl, n-octadecylsilyl, n-nonadecylsilyl, and n-eicosanylsilyl; monocycloalkylsilyl groups such as cyclopropylsilyl, cyclobutylsilyl, cyclopentylsilyl, cyclohexylsilyl, cycloheptylsilyl, cyclooctylsilyl, and cyclononylsilyl; monoarylsilyl groups such as phenylsilyl, 1 or 2-naphthylsilyl; and monoaralkylsilyl groups such as benzylsilyl, phenylethylsilyl, phenylpropylsilyl, 1 or 2-naphthylmethylsilyl.

The diorganosilyl group is preferably a group of $R_2SiH$ wherein R is independently as defined above, though not limited thereto. The preferred carbon count of R is the same as defined above for the alkoxy, aryloxy and aralkyloxy groups. Examples include straight or branched dialkylsilyl groups such as dimethylsilyl, diethylsilyl, di-n-propylsilyl, diisopropylsilyl, di-n-butylsilyl, diisobutylsilyl, di-m-butylsilyl, di-t-butylsilyl, di-n-pentylsilyl, di-n-hexylsilyl, di-n-heptylsilyl, di-n-octylsilyl, di-n-nonylsilyl, di-n-decylsilyl, di-n-undecylsilyl, di-n-dodecylsilyl, di-n-tridecylsilyl, di-n-tetradeylsilyl, di-n-pentadecylsilyl, di-n-hexadecylsilyl, di-n-heptadecylsilyl, di-n-octadecylsilyl, di-n-nonadecylsilyl, di-n-eicosanylsilyl, ethylmethylsilyl, isopropylmethylsilyl, and butylmethylsilyl; dicycloalkylsilyl groups such as dicyclopropylsilyl, dicyclobutylsilyl, dicyclopentylsilyl, dicyclohexylsilyl, dicycloheptylsilyl, dicyclooctylsilyl, dicyclononylsilyl, and cyclopentylcyclohexylsilyl; alkylarylsilyl groups such as methylphenylsilyl, ethylphenylsilyl, and n-propylphenylsilyl; diarylsilyl groups such as diphenylsilyl, bis(1 or 2-naphthyl)silyl, phenyl-1 or 2-naphthylsilyl; and diaralkylsilyl groups such as dibenzylsilyl, bis(phenylethyl)silyl, bis(phenylpropyl)silyl, bis(1 or 2-naphthylmethyl)silyl.

The triorganosilyl group is preferably a group of $R_3Si$ wherein R is independently as defined above, though not limited thereto. The preferred carbon count of R is the same as defined above for the alkoxy, aryloxy and aralkyloxy groups. Examples include straight or branched trialkylsilyl groups such as trimethylsilyl, triethylsilyl, tri-n-propylsilyl, triisopropylsilyl, tri-n-butylsilyl, triisobutylsilyl, tri-s-butylsilyl, tri-t-butylsilyl, tri-n-pentylsilyl, tri-n-hexylsilyl, tri-n-heptylsilyl, tri-n-octylsilyl, tri-n-nonylsilyl, tri-n-decylsilyl, tri-n-undecylsilyl, tri-n-dodecylsilyl, tri-n-tridecylsilyl, tri-n-tetradeylsilyl, tri-n-pentadecylsilyl, tri-n-hexadecylsilyl, tri-n-heptadecylsilyl, tri-n-octadecylsilyl, tri-n-nonadecylsilyl, tri-n-eicosanylsilyl, ethyldimethylsilyl, diisopropylmethylsilyl, and dibutylmethylsilyl; tricycloalkylsilyl groups such as tricyclopropylsilyl, tricyclobutylsilyl, tricyclopentylsilyl, tricyclohexylsilyl, tricycloheptylsilyl, tricyclooctylsilyl, and tricyclononylsilyl; alkylarylsilyl groups such as methyldiphenylsilyl, ethyldiphenylsilyl, and n-propyldiphenylsilyl; triarylsilyl groups such as triphenylsilyl, tri(1 or 2-naphthyl)silyl, diphenyl-1 or 2-naphthylsilyl; and triaralkylsilyl groups such as tribenzylsilyl, tri(phenylethyl)silyl, tri(phenylpropyl)silyl, tri(1 or 2-naphthylmethyl)silyl.

With respect to the foregoing substituent groups, at least one hydrogen atom on R may be substituted by a substituent X. Suitable substituents X include halogen, organoxy, monoorganoamino, diorganoamino, and organothio groups, and examples of the organoxy, monoorganoamino, diorganoamino, and organothio groups are as exemplified above.

Exemplary of the halogen are fluorine, chlorine, bromine and iodine, with fluorine being preferred. Suitable fluorine-substituted alkyl groups include trifluoropropyl, nonafluorohexyl and heptadecylfluorodecyl.

Of the foregoing substituent groups, $R^1$ to $R^6$ are each independently selected preferably from $C_1$-$C_{30}$ alkyl, $C_6$-$C_{30}$ aryl, and $C_7$-$C_{30}$ aralkyl groups which may be substituted with X, more preferably from $C_1$-$C_{10}$ alkyl and $C_6$-$C_{10}$ aryl groups.

When a pair of any one of $R^1$ to $R^3$ and any one of $R^4$ to $R^6$, taken together, represent a crosslinking substituent, the crosslinking substituent is not particularly limited as long as it is capable of crosslinking two silicon atoms. Exemplary crosslinking substituents include —O—, —S—, —NH—, —NR— wherein R is as defined above, —PR— wherein R is as defined above, —NH—$(CH_2)_k$—NH— wherein k is an integer of 1 to 10, —NR—$(CH_2)_k$—NR— wherein k is as defined above and R is independently as defined above, —PH—$(CH_2)_k$—PH— wherein k is as defined above, —PR—$(CH_2)_k$—PR— wherein k is as defined above and R is independently as defined above, —C≡C—, $C_1$-$C_{10}$ alkylene, $C_6$-$C_{30}$ arylene, $C_7$-$C_{30}$ aralkylene, —$(CH_2O)_k$— wherein k is as defined above, —$(CH_2O)_k$—O—$(CH_2)_k$— wherein k is independently as defined above, —O—$(CH_2O)_k$—O— wherein k is as defined above, —R'—O—$(CH_2O)_k$—O—

R'— wherein R' is each independently a $C_1$-$C_{10}$ alkylene group, $C_6$-$C_{30}$ arylene group or $C_7$-$C_{30}$ aralkylene group and k is as defined above, —$(CH_2S)_k$— wherein k is as defined above, —$(CH_2)_k$—S—$(CH_2)_k$— wherein k is independently as defined above, —S—$(CH_2)_k$—S— wherein k is as defined above, —R'—S—$(CH_2)_k$—O—R'— wherein R' is independently as defined above and k is as defined above, —$SiR_2$— wherein R is independently as defined above, and —$(CH_2)_k$—$SiR_2$—$(CH_2)_k$— wherein R is independently as defined above and k is independently as defined above.

Suitable $C_1$-$C_{10}$ alkylene groups include methylene, ethylene, propylene, trimethylene, tetramethylene, pentamethylene, and hexamethylene.

Suitable $C_6$-$C_{30}$ arylene groups include o-phenylene (1,2-phenylene), 1,2-naphthylene, 1,8-naphthylene, and 2,3-naphthylene.

Suitable $C_7$-$C_{30}$ aralkylene groups include —$(CH_2)_k$—Ar—wherein Ar is a $C_6$-$C_{20}$ arylene group and k is as defined above, —Ar—$(CH_2)_k$— wherein Ar and k are as defined above, and —$(CH_2)_k$—Ar—$(CH_2)_k$— wherein Ar is as defined above and k is independently as defined above.

Notably, in the foregoing alkylene, arylene and aralkylene groups, at least one hydrogen atom may be substituted by a substituent X wherein X is as defined above.

Assume that Z stands for a crosslinking substituent. Since the number of Z linking two silicon atoms is 1 to 3, the mononuclear iron complex having a crosslinking substituent Z is represented by the following formulae.

[Chemical Formula 4]

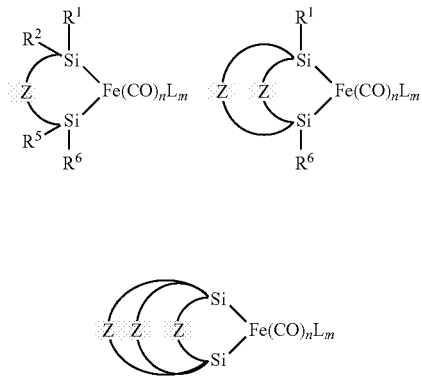

Herein $R^1$, $R^2$, $R^5$, $R^6$, L, n and m are as defined above, and Z is a crosslinking substituent.

Illustrative examples of the disilametallacycle structure having a crosslinking substituent include those of the following formulae, but are not limited thereto.

[Chemcial Formula 5]

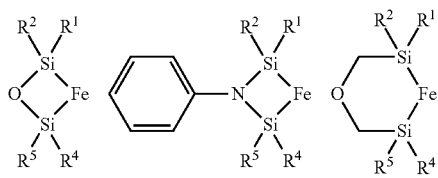

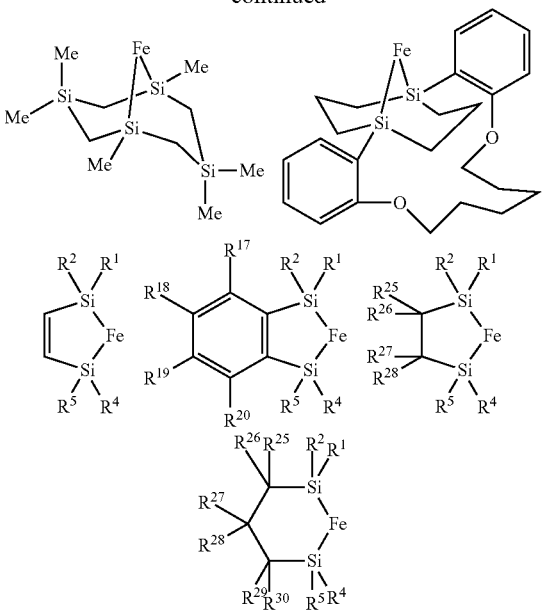

Herein Me stands for methyl.

In the above formulae, $R^1$, $R^2$, $R^4$ and $R^5$ are as defined above, $R^{17}$ to $R^{20}$ (substituent Y) are each independently hydrogen, halogen, $C_1$-$C_{10}$ alkyl, or $C_1$-$C_{10}$ alkoxy group, $R^{25}$ to $R^{30}$ are each independently hydrogen or a substituted or unsubstituted, $C_1$-$C_{20}$ monovalent hydrocarbon group. Preferably $R^{17}$ to $R^{20}$ and $R^{25}$ to $R^{30}$ are hydrogen.

Suitable monovalent hydrocarbon groups include alkyl, aryl and aralkyl groups, examples of which are as exemplified above.

Examples of the alkyl group, alkoxy group and halogen are as exemplified above.

L is a two-electron ligand other than CO, wherein two electrons coordinate with iron.

The two-electron ligand is not particularly limited as long as CO is excluded. Use may be made of any ligands which are conventionally used as the two-electron ligand in metal complexes, exclusive of CO. Typical ligands include compounds of nitrogen, phosphorus, oxygen, sulfur, and other elements containing an unshared electron pair (unpaired electron) such as amine, imine, nitrogen-containing heterocycle, phosphine, arsine, alcohol, thiol, ether, and sulfide; compounds containing π-electron such as alkene and alkyne; compounds containing both unpaired electron and π-electron such as aldehyde, ketone, nitrile, and isonitrile; molecular hydrogen (σ-electron in H—H bond coordinates) and hydrosilane (σ-electron in Si—H bond coordinates) capable of bonding by agostic interaction.

Included in the amine are tertiary amines represented by $R_3N$ wherein R is each independently as defined above.

Included in the imine are those represented by RC(=NR)R wherein R is each independently as defined above.

Examples of the nitrogen-containing heterocycle include pyrrole, imidazole, pyridine, pyrimidine, oxazoline, and isooxazoline.

Examples of the phosphine include those of $R_3P$ wherein R is each independently as defined above.

Examples of the arsine include those of $R_2As$ wherein R is each independently as defined above.

Examples of the alcohol include those of ROH wherein R is as defined above.

Included in the thiol are those obtained by substituting sulfur atom for oxygen atom of the above alcohols.

Included in the ether are those represented by ROR wherein R is each independently as defined above.

Included in the sulfide are those obtained by substituting sulfur atom for oxygen atom of the above ethers.

Included in the ketone are those represented by RCOR wherein R is each independently as defined above.

Included in the isonitrile are those represented by RNC wherein R is each independently as defined above.

Included in the alkene are those of 2 to 30 carbon atoms such as ethene, propene, 1-butene, 2-butene, 1-pentene, 2-pentene, cyclopentene, 1-hexene, cyclohexene, 1-heptene, 1-octene, 1-nonene, and 1-decene.

Included in the alkyne are those of 2 to 30 carbon atoms such as ethyne, propyne, 1-butyne, 2-butyne, 1-pentyne, 2-pentyne, 1-hexyne, 1-heptyne, 1-octyne, 1-nonyne, and 1-decyne.

Examples of the hydrosilane include triorganohydrosilanes, specifically tri($C_1$-$C_{30}$ organo)hydrosilanes, for example, those of $R^1R^2R^3SiH$ wherein $R^1$ to $R^3$ are as defined above.

Of the foregoing, the two-electron ligand L is preferably molecular hydrogen, amine, imine, nitrogen-containing heterocycle, phosphine, arsine, alcohol, thiol, ether, sulfide, nitrile, isonitrile, aldehyde, ketone, $C_2$-$C_{30}$ alkene, $C_2$-$C_{30}$ alkyne, or triorganohydrosilane.

Where two L's are present, they may bond together to form a ligand containing two coordinating two-electron functional groups. Typical examples include, but are not limited to, ethylenediamine, ethylene glycol dimethyl ether, 1,3-butadiene, and those of the formulae shown below.

In the mononuclear iron complex, it is excluded that where three L's are present, all they bond together to form a ligand containing three coordinating two-electron functional groups.

[Chemical Formula 6]

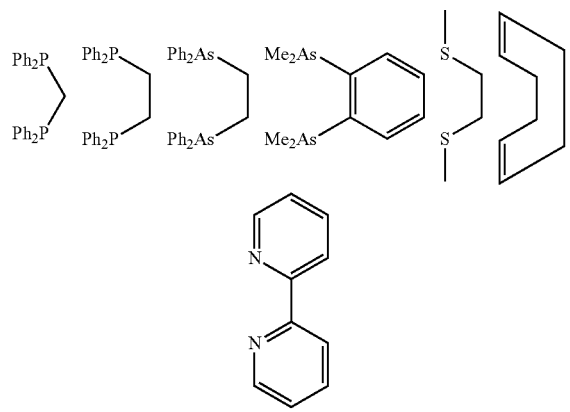

Herein Me stands for methyl, and Ph for phenyl.

In the mononuclear iron complex, the coordination number m of two-electron ligand L is an integer of 1 to 3, preferably 2.

The sum of the coordination number n of CO and the coordination number m of L is equal to 3 or 4, preferably 4.

Herein, a two-electron ligand L which forms a relatively weak bond with iron is advantageous in terms of catalytic activity. Among the above examples, L is more preferably a thiol, sulfide, or triorganohydrosilane, and even more preferably two triorganohydrosilanes of $SiHR^7R^8R^9$ and $SiHR^{10}R^{11}R^{12}$ wherein $R^7$ to $R^{12}$ are each independently an alkyl, aryl or aralkyl group which may be substituted with X which is as defined above, and two sulfides or thiols of $SR^{13}R^{14}$ and $SR^{15}R^{16}$ wherein $R^{13}$ to $R^{16}$ are each independently hydrogen, or an alkyl, aryl or aralkyl group which may be substituted with X which is as defined above.

Examples of the alkyl, aryl and aralkyl group are the same as exemplified above, while $C_1$-$C_{10}$ alkyl, $C_6$-$C_{20}$ aryl and $C_7$-$C_{20}$ aralkyl groups are preferred, and $C_1$-$C_{10}$ alkyl and $C_6$-$C_{20}$ aryl groups are more preferred.

When L's are triorganohydrosilanes of $SiHR^7R^8R^9$ and $SiHR^{10}R^{11}R^{12}$ wherein $R^7$ to $R^{12}$ are as defined above, at least two of four silicon atoms in the mononuclear iron complex may be linked by the crosslinking substituent Z. A combination of silicon atoms may be either a combination of silicon atoms having a silicon-iron covalent bond, a combination of silicon atoms in Si—H coordination, or a combination of a silicon-iron covalent bond with a silicon atom in Si—H coordination. Herein, the number of Z linking two silicon atoms is 1 to 3 whereas the total number of Z in the overall complex is 1 to 12.

When a mononuclear iron complex having crosslinking substituent Z is represented by a single coordination geometry, exemplary geometries are those of the following formulae, but not limited thereto. As alluded to previously, there are present coordination geometry isomers other than the illustrated ones, and in such cases, similar geometries having crosslinking substituent Z are present.

[Chemical Formula 7]

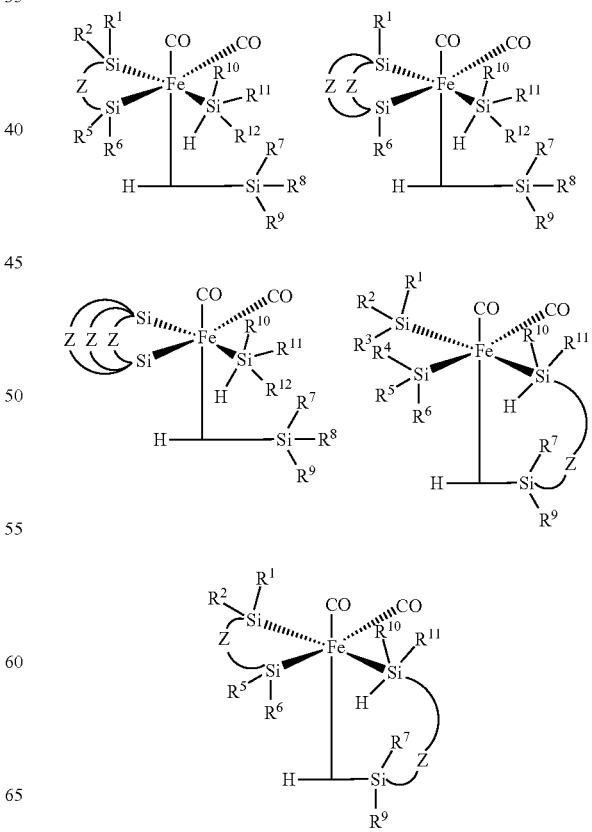

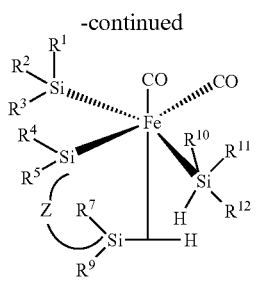

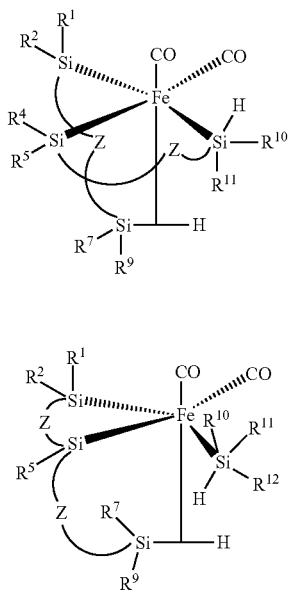

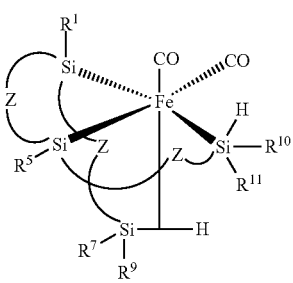

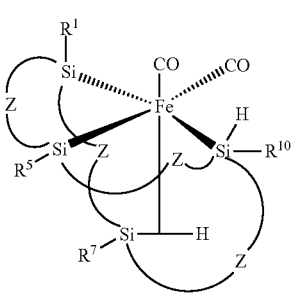

Herein $R^1$ to $R^{12}$ and are as defined above.

Exemplary geometries of the mononuclear iron complex having disilametallacycle structure include those of the following formulae (depicted with CO omitted), but are not limited thereto.

[Chemical Formula 8]

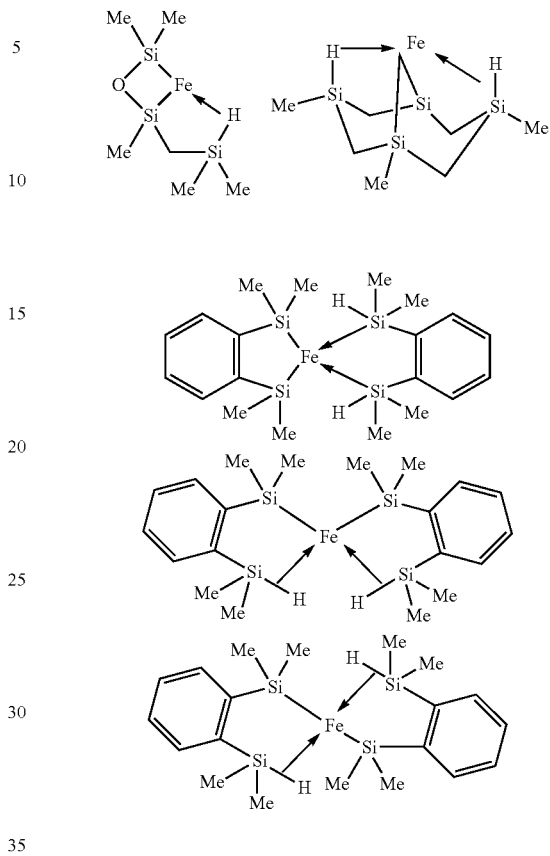

Herein Me stands for methyl.

When L's are two sulfides or thiols of $SR^{13}R^{14}$ and $SR^{15}R^{16}$ wherein $R^{13}$ to $R^{16}$ are as defined above, two sulfur atoms in the mononuclear iron complex may be linked by the crosslinking substituent Z.

When a mononuclear iron complex having crosslinking substituent Z is represented by a single coordination geometry, exemplary geometries are those of the following formulae, but not limited thereto. As alluded to previously, there are present coordination geometry isomers other than the illustrated ones, and in such cases, similar geometries having crosslinking substituent Z are present.

In these cases, two silicon atoms in the mononuclear iron complex may be linked by the crosslinking substituent Z.

[Chemical Formula 9]

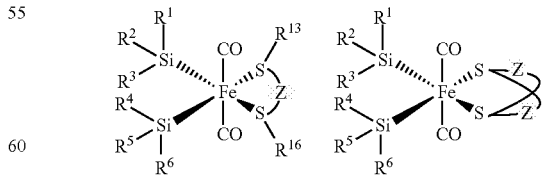

Herein $R^1$ to $R^6$, $R^{13}$, $R^{16}$ and Z are as defined above.

Exemplary geometries of the dithia(dithio) metallacycle structure include those of the following formulae, but are not limited thereto.

[Chemical Formula 10]

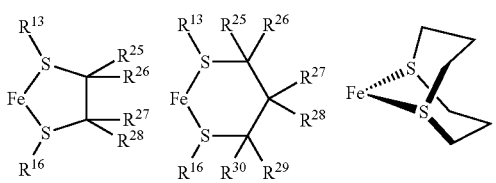

Herein $R^{13}$, $R^{16}$, $R^{25}$ to $R^{30}$ are as defined above.

Exemplary geometries of the mononuclear iron complex having dithiametallacycle structure include those of the following formulae, but are not limited thereto.

[Chemical Formula 11]

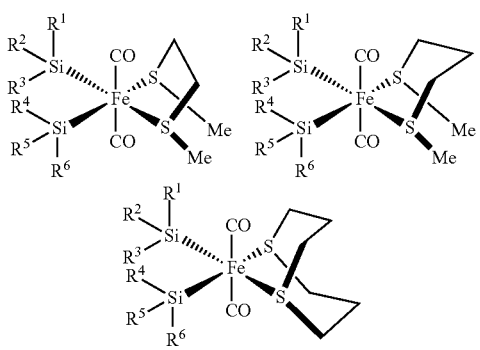

Herein $R^1$ to $R^6$ are as defined above and Me stands for methyl.

Especially preferred in the invention are mononuclear iron complexes having two CO's coordinated and triorganohydrosilanes (as two-electron ligand) in agostic Si—H bond coordination. When such an iron complex is represented for convenience sake by a single coordination geometry, exemplary geometries are those of formula (2). As alluded to previously, other coordination geometry isomers are acceptable.

[Chemical Formula 12]

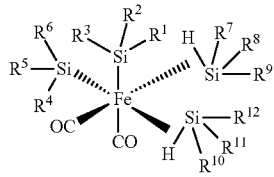

(2)

Herein $R^1$ to $R^{12}$ are as defined above. Preferably $R^1$ to $R^6$ are each independently an alkyl, aryl or aralkyl group which may be substituted with X which is as defined above.

Examples of the alkyl, aryl and aralkyl groups are the same as exemplified above, while $C_1$-$C_{10}$ alkyl, $C_6$-$C_{20}$ aryl and $C_7$-$C_{20}$ aralkyl groups are preferred, and $C_1$-$C_{10}$ alkyl and $C_6$-$C_{20}$ aryl groups are more preferred.

In formula (2) as well, at least two of four silicon atoms in the mononuclear iron complex may be linked by the crosslinking substituent. Specifically, at least one pair of any one of $R_1$ to $R^3$ and any one of $R^4$ to $R^6$ or any one of $R^7$ to $R^9$, or at least one pair of any one of $R^{10}$ to $R^{12}$ and any one of $R^4$ to $R^6$ or any one of $R^7$ to $R^9$ may bond together to form a crosslinking substituent such as alkylene, arylene or aralkylene. Alternatively, at least one pair of any one of $R^1$ to $R^3$ and any one of $R^4$ to $R^6$ or any one of $R^7$ to $R^9$ may bond together to form a crosslinking substituent such as alkylene, arylene or aralkylene, and at least one pair of any one of $R^{10}$ to $R^{12}$ and any one of $R^4$ to $R^6$ or any one of $R^7$ to $R^9$ may bond together to form a crosslinking substituent such as alkylene, arylene or aralkylene.

Examples of the alkylene, arylene and aralkylene groups are the same as exemplified above, while $C_1$-$C_{10}$ alkylene, $C_7$-$C_{20}$ arylene and $C_7$-$C_{20}$ aralkylene groups are preferred, and $C_1$-$C_6$ alkylene and $C_7$-$C_{20}$ arylene groups are more preferred.

Also useful are mononuclear iron complexes having two CO's coordinated and two sulfides or thiols (as two-electron ligand) coordinated. When such an iron complex is represented for convenience sake by a single coordination geometry, exemplary geometries are those of formula (3). As alluded to previously, other coordination geometry isomers are acceptable.

[Chemical Formula 13]

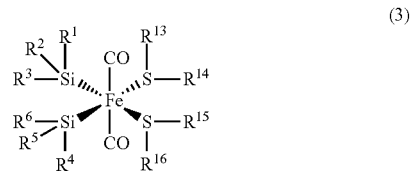

(3)

In formula (3), $R^1$ to $R^6$ and $R^{13}$ to $R^{16}$ are as defined above. Preferably $R^{13}$ to $R^{16}$ are each independently an alkyl, aryl or aralkyl group which may be substituted with X which is as defined above.

Examples of the alkyl, aryl and aralkyl groups are the same as exemplified above, while $C_1$-$C_{10}$ alkyl, $C_6$-$C_{20}$ aryl and $C_7$-$C_{20}$ aralkyl groups are preferred, and $C_1$-$C_{10}$ alkyl and $C_6$-$C_{20}$ aryl groups are more preferred.

In formula (3) as well, two sulfur atoms in the mononuclear iron complex may be linked by the crosslinking substituent. Specifically, at least one pair of either one of $R^{13}$ and $R^{14}$ and either one of $R^{15}$ and $R^{16}$ may bond together to form a crosslinking substituent such as alkylene, arylene or aralkylene.

In this case, two silicon atoms in the mononuclear iron complex may be linked by the crosslinking substituent. Specifically, at least one pair of any one of $R^1$ to $R^3$ and any one of $R^4$ to $R^6$ may bond together to form a crosslinking substituent such as alkylene, arylene or aralkylene.

Examples of the alkylene, arylene and aralkylene groups are the same as exemplified above, while $C_1$-$C_{10}$ alkylene, $C_7$-$C_{20}$ arylene and $C_7$-$C_{20}$ aralkylene groups are preferred, and $C_1$-$C_6$ alkylene and $C_7$-$C_{20}$ arylene groups are more preferred.

When the preferred mononuclear iron complex which can be used herein is represented by a single coordination geometry, exemplary geometries are those of formulae (4) and (5), more specifically formulae (6) and (7). As alluded to previously, other coordination geometry isomers are acceptable.

[Chemical Formula 14]

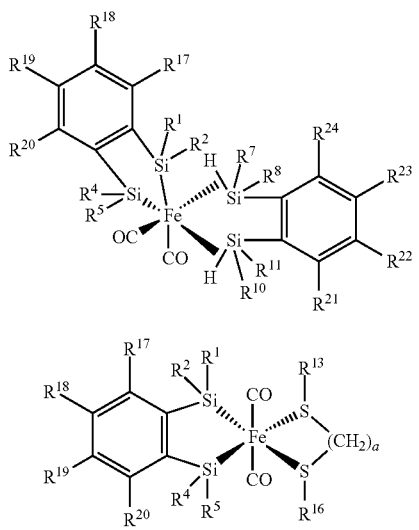

Herein, $R^1$, $R^2$, $R^4$, $R^5$, $R^7$, $R^8$, $R^{10}$, $R^{11}$, $R^{13}$, and $R^{16}$ to $R^{20}$ are as defined above, and $R_{21}$ to $R^{24}$ are as defined for $R^{17}$.

In formula (5), "a" is an integer of 1 to 6, preferably 2 or 3.

[Chemical Formula 15]

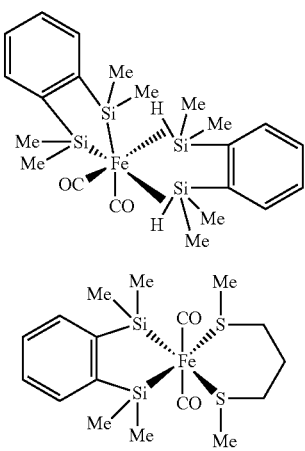

Herein Me stands for methyl.

The mononuclear iron complex of the invention may be prepared by any combination of well-known organic synthetic reactions.

For example, the iron complex having formula (4) may be obtained by irradiating with light an iron-carbonyl complex having a cycloalkadienyl group such as cyclohexadienyl or cyclooctadienyl as a ligand and a bissilyl compound such as 1,2-bis(dimethylsilyl)benzene in an inert gas atmosphere such as argon gas.

In this case, the amount of the bissilyl compound used may be about 1 to 10 moles, preferably 2 to 5 moles per mole of the iron-carbonyl complex.

As the organic solvent, any solvents may be used as long as they do not adversely affect the reaction. Suitable solvents used herein include aliphatic hydrocarbons such as pentane, hexane, heptane, octane, and cyclohexane; ethers such as diethyl ether, diisopropyl ether, dibutyl ether, cyclopentyl methyl ether, tetrahydrofuran, and 1,4-dioxane; and aromatic hydrocarbons such as benzene, toluene, xylene and mesitylene.

The reaction temperature may be set as appropriate in the range from the melting point to the boiling point of the organic solvent, preferably in the range of 10 to 50° C., and more preferably 15 to 30° C.

The reaction time is typically about 1 to about 48 hours.

After the completion of reaction, the solvent is distilled off, whereupon the target compound may be isolated by well-known purifying means such as recrystallization. Without isolation, the iron complex as prepared may be used as a catalyst for the intended reaction.

Also, the iron complex having a sulfide ligand as represented by formula (5) may be prepared by starting with the iron complex of formula (4) obtained by the above method, for example, and reacting it with a dithia hydrocarbon compound (e.g., 2,6-dithiaheptane) or a thiol compound (e.g., 1,3-propanedithiol) in an organic solvent as exemplified above in an inert gas atmosphere such as argon gas.

In this case, the amount of the dithia hydrocarbon compound used may be about 1 to 3 moles, preferably 1 to 1.5 moles, and more preferably 1 to 1.2 moles per mole of the iron complex.

The reaction temperature may be set as appropriate in the range from 0° C. to the boiling point of the organic solvent, preferably in the range of 10 to 50° C., and more preferably 15 to 30° C.

The reaction time is typically about 1 to about 48 hours.

After the completion of reaction, the solvent is distilled off, whereupon the target compound may be isolated by well-known purifying means such as recrystallization. Without isolation, the iron complex as prepared may be used as a catalyst for the intended reaction.

As alluded to previously, the mononuclear iron complex of the invention displays catalytic activity to three reactions: hydrosilylation reaction, hydrogenation reaction, and reductive reaction of carbonyl compounds.

For hydrosilylation reaction between a compound having an aliphatic unsaturated bond such as an olefin, silane or organopolysiloxane compound and a compound having a Si—H bond such as a silane or organopolysiloxane compound in the presence of the inventive mononuclear iron complex as catalyst, the amount of the catalyst used, though not particularly limited, is preferably at least 0.5 mol % when it is taken into account that the target compound is obtained in high yields by driving reaction under mild conditions at room temperature to about 100° C.

When an olefin compound having an aliphatic unsaturated bond is reduced with hydrogen gas in the presence of the inventive mononuclear iron complex as catalyst, to produce a saturated compound, the amount of the catalyst used, though not particularly limited, is preferably at least 1 mol % when it is taken into account that the target compound is obtained in high yields by driving reaction under mild conditions at room temperature and a hydrogen pressure of about 1 atm.

In either of the reactions, the upper limit of the amount of the catalyst used is about 10 mol % from the economic aspect, though not critical.

Also, when a carbonyl compound is reduced with a silane or siloxane compound having a Si—H group in the presence of the inventive mononuclear iron complex as catalyst, the amount of the catalyst used, though not particularly limited, is preferably at least 0.01 mol % when it is taken into account that the target compound is obtained in high yields by driving reaction under mild conditions. The upper limit of the amount of the catalyst used is about 5 mol % from the economic aspect, though not critical.

Examples of the carbonyl compound which can be subjected to reductive reaction include compounds having an amide, aldehyde, ketone, ester, carboxylic acid, and carboxylic acid salt (e.g., sodium or potassium salt) group. The carbonyl compound can be converted to a corresponding amine or alcohol compound by reacting it with a silane or siloxane having a Si—H group in the presence of the inventive iron complex catalyst.

EXAMPLES

Examples of the invention are given below by way of illustration and not by way of limitation.

For synthesis of iron complexes, a Schlenk system or glovebox was used, and all steps were performed in nitrogen or argon atmosphere. All the solvents used in the preparation of iron compounds were deoxygenated and dried by well-known techniques prior to use.

Hydrosilylation reaction of alkene, reductive reaction of amide, and solvent purification were all performed in an inert gas atmosphere. All the solvents and ingredients used in these reactions were purified, dried and deoxygenated by well-known techniques prior to use.

Analysis of $^1H$, $^{13}C$ and $^{29}Si$-NMR was performed by JNM-ECA600 and JNM-LA400 (JEOL Ltd.); IR spectroscopy by FT/IR-550 (JASCO Corp.); elemental analysis by 2400II/CHN (Perkin Elmer); X-ray crystallography by Vari-Max (Rigaku Corp.) with MoK α-ray of 0.71069 angstrom.

It is noted that in the chemical structural formulae shown below, hydrogen atoms are omitted according to the standard nomenclature. Me stands for methyl.

(1) Synthesis of Iron Complex

Example 1

Synthesis of Iron Complex A

Figure 2:
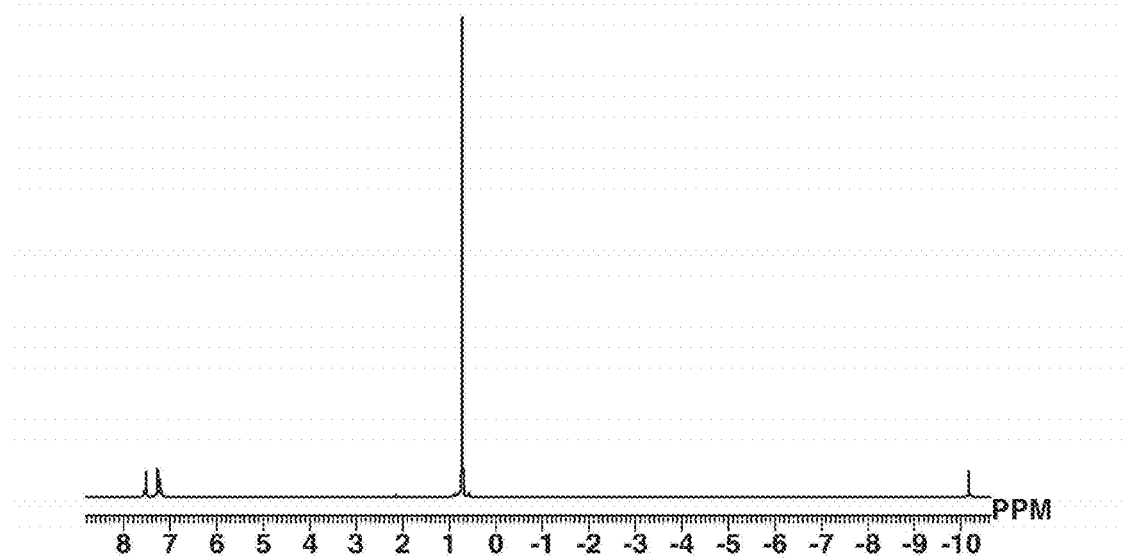
FIG. 2 is a diagram showing $^1$H-NMR spectrum of iron complex A in Example 1.
Figure 3:
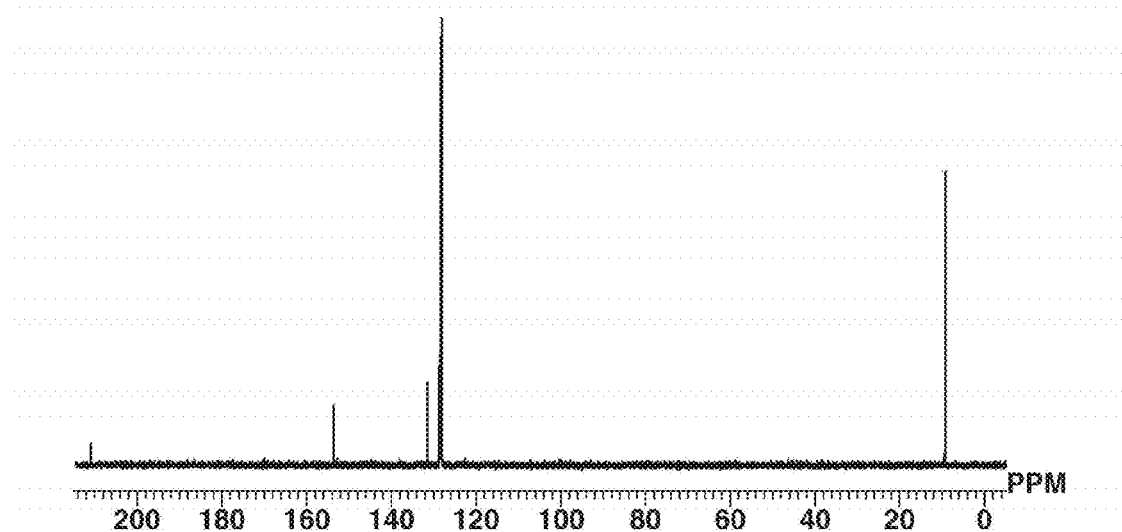
FIG. 3 is a diagram showing $^{13}$C-NMR spectrum of iron complex A in Example 1.

A 100-mL Schlenk tube under argon atmosphere was charged with ($\eta^4$-1,3-cyclohexadiene)iron(0) tricarbonyl complex (1.0 g, 4.50 mmol) and 1,2-bis(dimethylsilyl)benzene (1.92 g, 9.88 mmol), to which hexane (50 mL) which had been deaerated and dried was added. Under light irradiation using a high-pressure mercury lamp (UM-453B-A, 450 W, by Ushio Inc.), the contents were stirred at room temperature for 22 hours. After the completion of reaction, the reaction mixture was dried in vacuum. The dry product was dissolved in hexane (40 mL), from which a small amount of black insoluble matter as by-product was removed by centrifugation. Thereafter, the hexane solution was concentrated under reduced pressure to about 10 mL. Subsequent recrystallization at −35° C. yielded iron complex A (1.05 g, 2.11 mmol, 47%) typically represented by formula (6). For the resulting iron complex A, the geometry is shown in FIG. 1, the measurement results of $^1H$-NMR in FIG. 2, and the measurement results of $^{13}C$-NMR in FIG. 3.

$^1H$ NMR (CDCl$_3$, 395 MHz): δ=−10.2 (s, Jsi-$_H$=13.2 Hz, 2H, Si—H), 0.74 (s, 24H, SiMe$_2$), 7.23-7.29 (m, 4H, C$_6$H$_4$), 7.51-7.56 (m, 4H, C$_6$H$_4$).

$^{13}C$ NMR (CDCl$_3$, 395 MHz): δ=9.5, 128.9, 131.7, 153.5, 210.8.

IR (KBr pellet): ν=1981 ($\nu_{Si-H}$), 1929 ($\nu_{Fe-CO}$) cm$^{-1}$

Anal. calcd. for C$_{22}$H$_{34}$O$_2$FeSi$_4$:
C, 52.99; H, 6.87 Found: C, 52.84; H, 6.77.

Example 2

Synthesis of Iron Complex B

Figure 4:
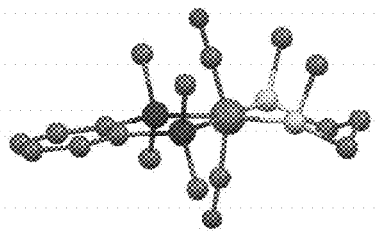
FIG. 4 illustrates the geometry of iron complex B obtained in Example 2.
Figure 5:
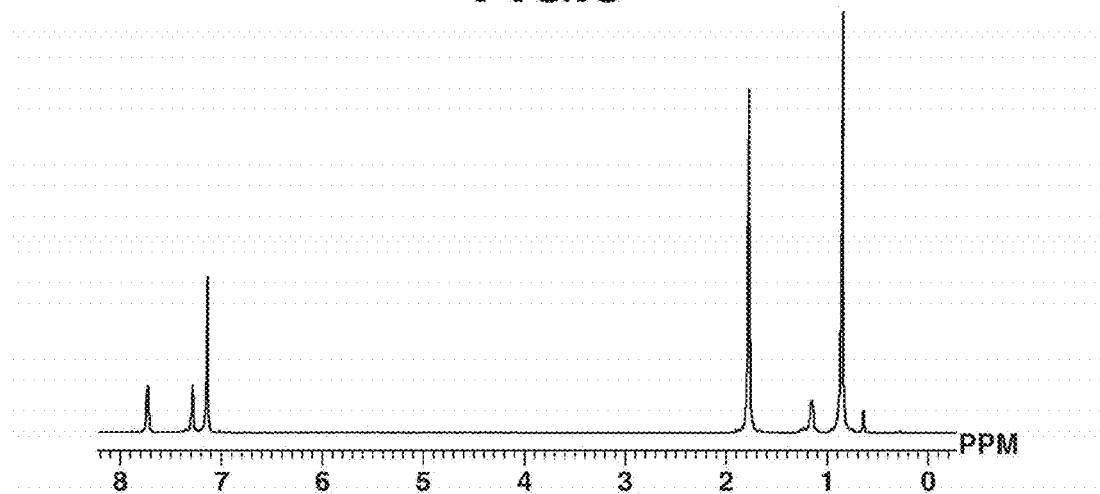
FIG. 5 is a diagram showing $^1$H-NMR spectrum of iron complex B in Example 2.
Figure 6:
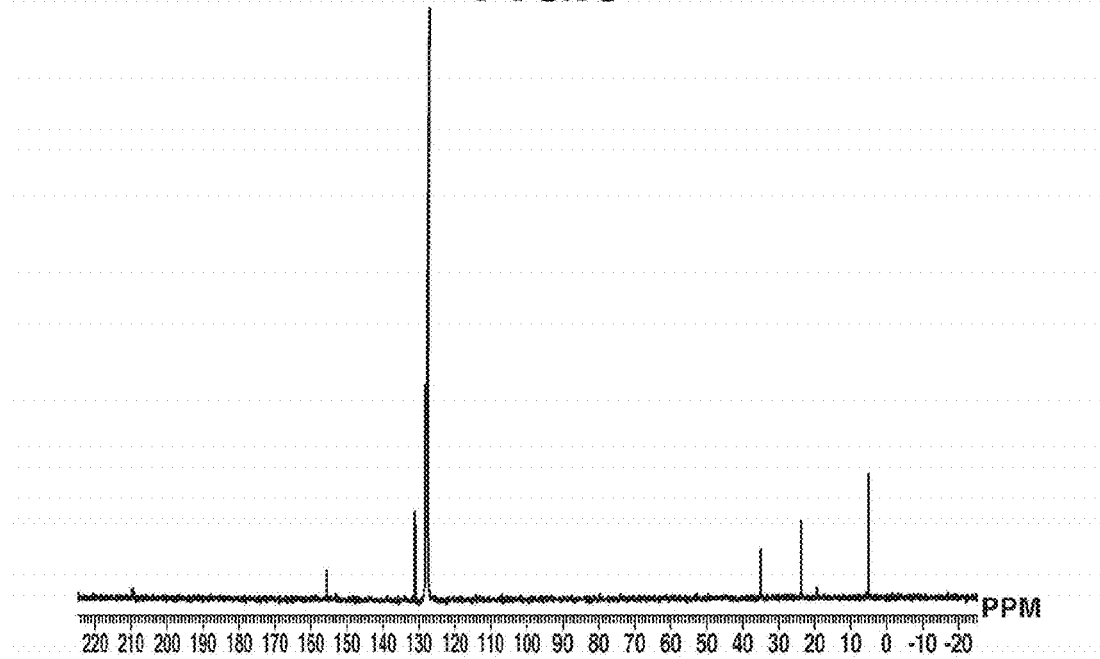
FIG. 6 is a diagram showing $^{13}$C-NMR spectrum of iron complex B in Example 2.

In a 50-mL Schlenk tube under argon atmosphere, iron complex A (200 mg, 0.40 mmol) was dissolved in toluene (20 mL) which had been deaerated and dried, to which 2,6-dithiaheptane (55 mg, 0.40 mmol) was added. The contents were stirred at room temperature for 12 hours. After the completion of reaction, the reaction mixture was dried in vacuum. The dry product was dissolved in diethyl ether (10 mL). Thereafter, the solution was concentrated under reduced pressure to about 5 mL. Subsequent recrystallization at −35° C. yielded iron complex B (163 mg, 0.37 mmol, 93%) typically represented by formula (7). For the resulting iron complex B, the geometry is shown in FIG. 4, the measurement results of $^1H$-NMR in FIG. 5, and the measurement results of $^{13}C$-NMR in FIG. 6.

$^1H$ NMR (600 MHz, C$_6$D$_6$): δ=0.89 (s, 12H, Si(C$\underline{H}_3$)$_2$), 1.17 (s, 2H, CH$_2$C$\underline{H}_2$CH$_2$), 1.79 (s, 10H, SCH$_3$ and SCH$_2$), 7.29 (bs, 2H, C$_6$H$_4$), 7.73 (bs, 2H, C$_6$H$_4$).

$^{29}Si$ NMR (119 MHz, C$_6$D$_6$): δ=40.90.

IR (KBr pellet): ν=1892, 1874 ($\nu_{Fe-CO}$) cm$^{-1}$

Anal. calcd. for C$_{17}$H$_{20}$O$_2$FeSi$_2$S$_2$:
C, 46.35; H, 6.41 Found: C, 46.21; H, 6.38.

(2) Hydrosilylation Reaction Using Iron Complex A

Example 3

Hydrosilylation of 2-octene with 1,1,1,3,3-pentamethyldisiloxane

A 20-mL Schlenk tube equipped with a magnetic stirrer was heat dried while pumping to a vacuum of 5 Pa before its interior was purged with argon atmosphere. Into the Schlenk tube, iron complex A (15 mg, 0.03 mmol) was admitted as catalyst. To the tube, 2-octene (156.3 μL, 1.0 mmol) was added, after which 1,1,1,3,3-pentamethyldisiloxane (195.2 μL, 1.0 mmol) was added. The solution was cooled, to which anisole (108.6 μL, 1.0 mmol, the amount used is identical hereinafter) was added as internal standard. By $^1H$-NMR spectroscopy, the geometry and yield of the product were determined. The reaction mixture was purified by distillation (8 Pa, 70° C.), obtaining the target compound (195 mg, 0.75 mmol). The resulting compound was identified for geometry by $^1H$, $^{13}C$, and $^{29}Si$-NMR spectroscopy. The results are shown as Entry 1 in Table 1.

$^1H$ NMR (400 MHz, CDCl$_3$): δ=0.03 (s, 6H, Si(C$\underline{H}_3$)$_2$), 0.06 (s, 9H, Si(C$\underline{H}_3$)$_3$), 0.45-0.55 (m, 2H, SiC$\underline{H}_2$), 0.88 (t, J$_{HH}$=7.2 Hz, 3H, CH$_2$C$\underline{H}_3$), 1.20-1.34 (m, 12H, (C$\underline{H}_2$)$_6$).

$^{13}C$ NMR (100 MHz, CDCl$_3$): δ=0.34, 1.98, 14.09, 18.42, 22.65, 23.23, 29.29, 29.36, 31.94, 33.37.

$^{29}Si$ NMR (119 MHz, CDCl$_3$): δ=6.98, 7.63.

HRMS (EI) calcd. for C$_{12}$H$_{32}$OSi$_2$-Me 245.1757. found 245.1759.

Example 4

Hydrosilylation of 2-octene with 1,1,1,3,5,5,5-heptamethyltrisiloxane

A 20-mL Schlenk tube equipped with a magnetic stirrer was heat dried while pumping to a vacuum of 5 Pa before its interior was purged with argon atmosphere. Into the Schlenk tube, iron complex A (15 mg, 0.03 mmol) was admitted as catalyst. To the tube, 2-octene (156.3 µL, 1.0 mmol) was added, after which 1,1,1,3,5,5,5-heptamethyltrisiloxane (271.4 µL, 1.0 mmol) was added. The solution was stirred at 80° C. for 3 hours. The solution was cooled, to which anisole was added as internal standard. By $^1$H-NMR spectroscopy, the geometry and yield of the product were determined. The reaction mixture was purified by distillation (5 Pa, 70° C.), obtaining the target compound (274 mg, 0.82 mol). The results are shown as Entry 2 in Table 1. The resulting compound was identified for geometry by $^1$H, $^{13}$C, and $^{29}$Si-NMR spectroscopy.

$^1$H NMR (600 MHz, CDCl$_3$): δ=0.01 (s, 3H, SiCH$_3$), 0.09 (s, 18H, (Si(CH$_3$)$_3$)$_2$), 0.42-0.47 (m, 2H, SiCH$_2$), 0.88 (t, $J_{HH}$=6.8 Hz, 3H, CH$_2$CH$_3$), 1.23-1.33 (m, 12H, (CH$_2$)$_6$).

$^{13}$C NMR (100 MHz, CDCl$_3$): δ=−0.26, 1.86, 14.11, 17.64, 22.67, 23.06, 29.25, 29.34, 31.93, 33.25.

$^{29}$Si NMR (119 MHz, CDCl$_3$): δ=−21.12, 6.78.

HRMS (EI) calcd. for C$_{16}$H$_{38}$O$_2$Si$_3$-Me 319.1945. found 319.1941.

Example 5

Hydrosilylation of 2-octene with triethoxysilane

A 20-mL Schlenk tube equipped with a magnetic stirrer was heat dried while pumping to a vacuum of 5 Pa before its interior was purged with argon atmosphere. Into the Schlenk tube, iron complex A (15 mg, 0.03 mmol) was admitted as catalyst. To the tube, 2-octene (156.3 µL, 1.0 mmol) was added, after which triethoxysilane (184.6 µL, 1.0 mmol) was added. The solution was stirred at 80° C. for 3 hours. The solution was cooled, to which anisole was added as internal standard substance. By $^1$H-NMR spectroscopy, the geometry and yield of the product were determined. The resulting compound was identified for geometry by $^1$H-NMR spectroscopy. The results are shown as Entry 3 in Table 1.

$^1$H NMR (400 MHz, CDCl$_3$): δ=0.63 (m, 2H, Si(CH$_2$)), 0.72 (t, 3H, CH$_3$), 1.15 (t, $J_{HH}$=7.2 Hz, 9H, Si(OCH$_2$CH$_3$)), 1.29 (m, 12H, CH$_2$), 3.73 (q, $J_{HH}$=7.2 Hz, 9H, Si(OCH$_2$CH$_3$)).

Example 6

Hydrosilylation of 2-octene with triethylsilane

A 20-mL Schlenk tube equipped with a magnetic stirrer was heat dried while pumping to a vacuum of 5 Pa before its interior was purged with argon atmosphere. Into the Schlenk tube, iron complex A (15 mg, 0.03 mmol) was admitted as catalyst. To the tube, 2-octene (156.3 µL, 1.0 mmol) was added, after which triethylsilane (159.6 µL, 1.0 mmol) was added. The solution was cooled, to which anisole was added as internal standard. By $^1$H-NMR spectroscopy, the geometry and yield of the product were determined. The resulting compound was identified for geometry by $^1$H-NMR spectroscopy. The results are shown as Entry 4 in Table 1.

$^1$H NMR (400 MHz, CDCl$_3$): δ=0.51 (m, 8H, Si(CH$_2$) 4), 0.84-1.04 (m, 12H, Si(CH$_2$CH$_3$) and CH$_3$), 1.18-1.38 (m, 12H, CH$_2$).

TABLE 1

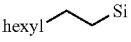

| Entry | Si—H | Yield$^a$ |
|---|---|---|
| 1 | TMSOSiMe$_2$H | 84 (75 $^b$) |
| 2 | (TMSO)$_2$SiMeH | 89 (82 $^b$) |
| 3 | (EtO)$_3$SiH | 6 |
| 4 | Et$_3$SiH | 36 |

[a] The yield was determined by $^1$H NMR analysis with anisole as an internal standard.
[b] Isolated yield.

Example 7

Hydrosilylation of 1-octene with 1,1,1,3,3-pentamethyldisiloxane

A 20-mL Schlenk tube equipped with a magnetic stirrer was heat dried while pumping to a vacuum of 5 Pa before its interior was purged with argon atmosphere. Into the Schlenk tube, iron complex A (15 mg, 0.03 mmol) was admitted as catalyst. To the tube, 1-octene (156.3 µL, 1.0 mmol) was added, after which 1,1,1,3,3-pentamethyldisiloxane (195.2 µL, 1.0 mmol) was added. The solution was stirred at 80° C. for 3 hours. The solution was cooled, to which anisole was added as internal standard. By $^1$H-NMR spectroscopy, the geometry and yield of the product were determined. The results are shown as Entry 1 in Table 2.

$^1$H NMR (400 MHz, CDCl$_3$): δ=0.03 (s, 6H, Si(CH$_3$)$_2$), 0.06 (s, 9H, Si(CH$_3$)$_3$), 0.45-0.55 (m, 2H, SiCH$_2$), 0.88 (t, $J_{HH}$=7.2 Hz, 3H, CH$_2$CH$_3$), 1.20-1.34 (m, 12H, (CH$_2$)$_6$).

Example 8

Hydrosilylation of 1-octene with 1,1,1,3,5,5,5-heptamethyltrisiloxane

A 20-mL Schlenk tube equipped with a magnetic stirrer was heat dried while pumping to a vacuum of 5 Pa before its interior was purged with argon atmosphere. Into the Schlenk tube, iron complex A (15 mg, 0.03 mmol) was admitted as catalyst. To the tube, 1-octene (156.3 µL, 1.0 mmol) was added, after which 1,1,1,3,5,5,5-heptamethyltrisiloxane (271.4 µL, 1.0 mmol) was added. The solution was stirred at 80° C. for 3 hours. The solution was cooled, to which anisole was added as internal standard. By $^1$H-NMR spectroscopy, the geometry and yield of the product were determined. The reaction mixture was purified by distillation (5 Pa, 70° C.), obtaining the purified product (244 mg, 0.73 mmol). The results are shown as Entry 2 in Table 2. The resulting compound was identified for geometry by $^1$H, $^{13}$C, and $^{29}$Si-NMR spectroscopy.

$^1$H NMR (600 MHz, CDCl$_3$): δ=|0.01 (s, 3H, SiCH$_3$), 0.09 (s, 18H, (Si(CH$_3$)$_3$)$_2$), 0.42-0.47 (m, 2H, SiCH$_2$), 0.88 (t, $J_{HH}$=6.8 Hz, 3H, CH$_2$CH$_3$), 1.23-1.33 (m, 12H, (CH$_2$)$_6$).

$^{13}$C NMR (100 MHz, CDCl$_3$): δ=−0.26, 1.86, 14.11, 17.64, 22.67, 23.06, 29.25, 29.34, 31.93, 33.25.

$^{29}$Si NMR (119 MHz, CDCl$_3$): δ=−21.12, 6.78.

HRMS (EI) calcd. for C$_{16}$H$_{38}$O$_2$S$_8$-Me 319.1945. found 319.1941.

Example 9

Hydrosilylation of cyclopentene with 1,1,1,3,3-pentamethyldisiloxane

A 20-mL Schlenk tube equipped with a magnetic stirrer was heat dried while pumping to a vacuum of 5 Pa before its interior was purged with argon atmosphere. Into the Schlenk tube, iron complex A (25 mg, 0.05 mmol) was admitted as catalyst. To the tube, cyclopentene (44.2 μL, 0.5 mmol) was added, after which 1,1,1,3,3-pentamethyldisiloxane (97.6 μL, 0.5 mmol) was added. The solution was stirred at 80° C. for 3 hours. The solution was cooled, to which anisole was added as internal standard. By $^1$H-NMR spectroscopy, the geometry and yield of the product were determined. The results are shown as Entry 3 in Table 2.

$^1$H NMR (400 MHz, $C_6D_6$): δ=0.10 (s, 6H, SiC$\underline{H}_3$), 0.13 (s, 9H, (Si(C$\underline{H}_3$)$_3$), 0.81-0.93 (m, 1H, SiC$\underline{H}$(CH$_2$)$_2$), 1.28-1.40 (m, 2H, CH$_2$), 1.46-1.63 (m, 4H, CH$_2$), 1.65-1.79 (m, 2H, CH$_2$).

Example 10

Hydrosilylation of cyclopentene with 1,1,1,3,5,5,5-heptamethyltrisiloxane

A 20-mL Schlenk tube equipped with a magnetic stirrer was heat dried while pumping to a vacuum of 5 Pa before its interior was purged with argon atmosphere. Into the Schlenk tube, iron complex A (25 mg, 0.05 mmol) was admitted as catalyst. To the tube, cyclopentene (44.2 μL, 1.0 mmol) was added, after which 1,1,1,3,5,5,5-heptamethyltrisiloxane (135.7 μL, 1.0 mmol) was added. The solution was stirred at 80° C. for 3 hours. The solution was cooled, to which anisole was added as internal standard. By $^1$H-NMR spectroscopy, the geometry and yield of the product were determined. The reaction mixture was purified by distillation (5 Pa, room temperature), obtaining the purified product (226 mg, 0.78 mmol). The results are shown as Entry 4 in Table 2. The resulting compound was identified for geometry by $^1$H, $^{13}$C, and $^{29}$Si-NMR spectroscopy.

$^1$H NMR (600 MHz, $C_6D_6$): δ=0.23 (s, 3H, SiC$\underline{H}_3$), 0.28 (s, 18H, (Si(C$\underline{H}_3$)$_3$)$_2$), 0.96-1.05 (m, 1H, SiC$\underline{H}$(CH$_2$)$_2$), 1.54-1.65 (m, 4H, CH$_2$), 1.69-1.75 (m, 2H, CH$_2$), 1.86-1.92 (m, 2H, CH$_2$).

$^{13}$C NMR (150 MHz, CDCl$_3$): δ=−1.39, 2.19, 27.46, 27.66, 27.92.

$^{29}$Si NMR (119 MHz, CDCl$_3$): δ=−21.70, 6.59.

HRMS (EI) calcd. for $C_{12}H_{30}O_2Si_3$-Me 275.1319. found 275.1319.

Example 11

Hydrosilylation of Ethylene with Dimethylphenylsilane

A 20-mL Schlenk tube equipped with a magnetic stirrer was heat dried while pumping to a vacuum of 5 Pa before its interior was purged with argon atmosphere. Into the Schlenk tube, iron complex A (5 mg, 0.01 mmol) was admitted as catalyst and dissolved in toluene (2 mL). To the solution, dimethylphenylsilane (136 mg, 1.0 mmol) was added. The solution was freeze deaerated, after which the Schlenk tube was purged with ethylene atmosphere. The solution was stirred at room temperature for 16 hours. Toluene was distilled off in vacuum. By $^1$H-NMR spectroscopy, the geometry and yield of the product were determined. The resulting silane was identified for geometry by $_1$H and $^{13}$C-NMR spectroscopy. The results are shown as Entry 1 in Table 3.

$^1$H NMR (CDCl$_3$, 395 MHz): δ=0.25 (s, 6H, Si$\underline{Me}^2$), 0.73 (q, 2H, C$\underline{H}_2$), 0.96 (t, 3H, CH$_2$C$\underline{H}_3$), 7.31-7.38 (m, 3H, $C_6H_5$), 7.48-7.54 (m, 2H, $C_6H_5$).

$^{13}$C NMR (CDCl$_3$, 395 MHz): δ=−3.0, 7.9, 30.2, 128.2, 129.2, 134.1, 140.0.

Example 12

Hydrosilylation of ethylene with 1,1,1,3,3-pentamethyldisiloxane

A 20-mL Schlenk tube equipped with a magnetic stirrer was heat dried while pumping to a vacuum of 5 Pa before its interior was purged with argon atmosphere. Into the Schlenk tube, iron complex A (5 mg, 0.01 mmol) was admitted as catalyst and dissolved in toluene (2 mL). To the solution, 1,1,1,3,3-pentamethyldisiloxane (195.2 μL, 1.0 mmol) was added. The solution was freeze deaerated, after which the Schlenk tube was purged with ethylene atmosphere. The solution was stirred at room temperature for 16 hours. Toluene was distilled off in vacuum. By $^1$H-NMR spectroscopy, the geometry and yield of the product were determined. The reaction mixture was purified by distillation (5 Pa, room temperature), obtaining the purified product (160 mg, 0.91 mmol). The results are shown as Entry 2 in Table 3. The resulting silane was identified for geometry by $^1$H, $^{13}$C and $^{29}$Si-NMR spectroscopy.

$^1$H NMR (600 MHz, CDCl$_3$): δ=0.03 (s, 6H, Si(C$\underline{H}_3$)$_2$), 0.06 (s, 9H, Si(C$\underline{H}_3$)$_3$), 0.49 (q, $J_{HH}$=8.2 Hz, 2H, SiC$\underline{H}_2$CH$_3$), 0.92 (t, $J_{HH}$=8.2 Hz, 3H, SiCH$_2$C$\underline{H}_3$).

$^{13}$C NMR (100 MHz, CDCl$_3$): δ=−0.28, 1.93, 6.72, 10.03.

$^{29}$Si NMR (119 MHz, CDCl$_3$): δ=7.05, 8.60.

HRMS (EI) calcd. for $C_7H_{20}OSi_2$ 176.1053. found 176.1058.

TABLE 2

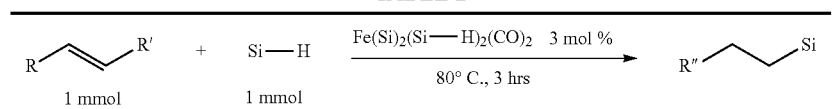

| Entry | Olefin | Si—H | Yield [a] |
|---|---|---|---|
| 1 | 1-octene | TMSOSiMe$_2$H | 80 |
| 2 | 1-octene | (TMSO)$_2$SiMeH | 82 (73 [b]) |
| 3 [c] | cyclopentene | TMSOSiMe$_2$H | 80 |
| 4 [c] | cyclopentene | (TMSO)$_2$SiMeH | 82 (78 [b]) |

[a] The yield was determined by $^1$H NMR analysis with anisole as an internal standard.
[b] Isolated yield.
[c] 10 mol % of catalyst was used.

Example 13

Hydrosilylation of ethylene with 1,1,1,3,5,5,5-heptamethyltrisiloxane

A 20-mL Schlenk tube equipped with a magnetic stirrer was heat dried while pumping to a vacuum of 5 Pa before its interior was purged with argon atmosphere. Into the Schlenk tube, iron complex A (5 mg, 0.01 mmol) was admitted as catalyst and dissolved in toluene (2 mL). To the solution, 1,1,1,3,5,5,5-heptamethyltrisiloxane (271.4 μL, 1.0 mmol) was added. The solution was freeze deaerated, after which the Schlenk tube was purged with ethylene atmosphere. The solution was stirred at room temperature for 16 hours. Toluene was distilled off in vacuum. By $^1$H-NMR spectroscopy, the geometry and yield of the product were determined. The reaction mixture was purified by distillation (5 Pa, room temperature), obtaining the purified product (234 mg, 0.93 mmol). The resulting silane was identified for geometry by $^1$H, $^{13}$C and $^{29}$Si-NMR spectroscopy. The results are shown as Entry 3 in Table 3.

$^1$H NMR (600 MHz, CDCl$_3$): δ=−0.003 (s, 3H, SiCH$_3$), 0.09 (s, 18H, (Si(CH$_3$)$_3$)$^2$), 0.43 (q, J$_{HH}$=7.7 Hz, 2H, SiCH$_2$CH$_3$), 0.91 (t, J$_{HH}$=7.7 Hz, 3H, SiCH$_2$CH$_3$).

$^{13}$C NMR (100 MHz, CDCl$_3$): δ=−0.96, 1.82, 6.59, 9.31.

$^{29}$Si NMR (119 MHz, CDCl$_3$): δ=−20.55, 6.98.

HRMS (EI) calcd. for C$_9$H$_{26}$O$_3$Si$_3$-Me 237.1006. found 235.1004.

Example 14

Hydrosilylation of Ethylene with Triethoxysilane

A 20-mL Schlenk tube equipped with a magnetic stirrer was heat dried while pumping to a vacuum of 5 Pa before its interior was purged with argon atmosphere. Into the Schlenk tube, iron complex A (5 mg, 0.01 mol) was admitted as catalyst and dissolved in toluene (2 mL). To the solution, triethoxysilane (184.6 μL, 1.0 mmol) was added. The solution was freeze deaerated, after which the Schlenk tube was purged with ethylene atmosphere. The solution was stirred at room temperature for 16 hours. Toluene was distilled off in vacuum. By $^1$H-NMR spectroscopy, the geometry and yield of the product were determined. The results are shown as Entry 4 in Table 3.

$^1$H NMR (C$_6$D$_6$, 400 MHz): δ=0.62 (q, 2H, J$_{HH}$=7.7 Hz, SiCH$_2$CH$_3$), 0.99 (t, 3H, J$_{HH}$=7.7 Hz, SiCH$_2$CH$_3$), 1.22 (t, 9H, J$_{HH}$=7.7 Hz, Si(OCH$_2$CH$_3$)$_3$), 3.82 (q, 6H, J$_{HH}$=7.7 Hz, Si(OCH$_2$CH$_3$)$_3$).

Example 15

Hydrosilylation of Ethylene with Triethylsilane

A 20-mL Schlenk tube equipped with a magnetic stirrer was heat dried while pumping to a vacuum of 5 Pa before its interior was purged with argon atmosphere. Into the Schlenk tube, iron complex A (5 mg, 0.01 mmol) was admitted as catalyst and dissolved in toluene (2 mL). To the solution, triethylsilane (184.6 μL, 1.0 mmol) was added. The solution was freeze deaerated, after which the Schlenk tube was purged with ethylene atmosphere. The solution was stirred at room temperature for 16 hours. Toluene was distilled off in vacuum. By $^1$H-NMR spectroscopy, the geometry and yield of the product were determined. The results are shown as Entry 5 in Table 3.

$^1$H NMR (C$_6$D$_5$, 400 MHz): δ=0.5 (q, 8H, J$_{HH}$=8.0 Hz, SiCH$_2$CH$_3$), 0.95 (t, 12H, J=8.0, SiCH$_2$CH$_3$).

TABLE 3

$$CH_2=CH_2 \text{ (1 atm)} + Si-H \text{ (1 mmol)} \xrightarrow[\text{toluene, r.t, 16 hrs}]{\text{Fe(Si)}_2(Si-H)_2(CO)_2 \text{ (X mol \%)}, \text{Ph-prz (2X mol \%)}} CH_3-CH_2-Si$$

| Entry | Si—H | X | Yield |
|---|---|---|---|
| 1 | Me$_2$PhSiH | 1 | 99 |
| 2 | TMSOSiMe$_2$H | 1 | 99 |
| 3 | (TMSO)$_2$SiMeH | 1 | 99 |
| 4 | (EtO)$_3$SiH | 10 | 99 |
| 5 | Et$_3$SiH | 5 | 92 |

(3) Hydrogenation Reaction Using Iron Complex A

Example 16

Hydrogenation of Styrene

A 20-mL Schlenk tube equipped with a magnetic stirrer was heat dried while pumping to a vacuum of 5 Pa before its interior was purged with argon atmosphere. Into the Schlenk tube, iron complex A (25 mg, 0.05 mmol) was admitted as catalyst and dissolved in toluene (2 mL). To the solution, styrene (114 μL, 1.0 mmol) was added. The solution was freeze deaerated, after which the Schlenk tube was purged with hydrogen atmosphere. The solution was stirred at room temperature for 3 hours. With anisole added as internal standard, the geometry and yield of the product were determined by $^1$H-NMR spectroscopy. The resulting compound was identified for geometry by $^1$H and $^{13}$C-NMR spectroscopy. The results are shown as Entry 1 in Table 4.

$^1$H NMR (CDCl$_3$, 395 MHz): δ=1.13 (t, J$_{HH}$=7.2 Hz, 3H, CH$_2$CH$_3$), 2.54 (q, J$_{HH}$=7.2 Hz, 2H, CH$_2$CH$_3$), 7.02-7.11 (m, 3H, C$_6$H$_5$), 7.11-7.20 (m, 2H, C$_6$H$_5$).

$^{13}$C NMR (100 MHz, CDCl$_3$): δ=15.6, 28.8, 125.6, 127.8, 128.3, 144.3.

Example 17

Hydrogenation of Trans-Stilbene

A 20-mL Schlenk tube equipped with a magnetic stirrer was heat dried while pumping to a vacuum of 5 Pa before its interior was purged with argon atmosphere. Into the Schlenk tube, iron complex A (25 mg, 0.05 mmol) was admitted as catalyst and dissolved in toluene (2 mL). To the solution, trans-stilbene (180 mg, 1.0 mmol) was added. The solution was freeze deaerated, after which the Schlenk tube was purged with hydrogen atmosphere. The solution was stirred at room temperature for 6 hours. With anisole added as internal standard, the geometry and yield of the product were determined by $^1$H-NMR spectroscopy. The solvent was distilled off in vacuum. The residual solid was purified by silica gel-packed column chromatography using hexane as developing solvent, obtaining dibenzyl (173 mg, 0.95 mmol, 95%). The resulting compound was identified for geometry by $^1$H and $^{13}$C-NMR spectroscopy. The results are shown as Entry 2 in Table 4.

$^1$H NMR (CDCl$_3$, 395 MHz): δ=2.93 (s, 4H, CH$_2$), 7.12-7.23 (m, 6H, C$_6$H$_5$), 7.24-7.32 (m, 4H, C$_6$H$_5$).

$^{13}$C NMR (CDCl$_3$, 100 MHz): δ=37.9, 125.9, 128.3, 128.5, 141.8.

Example 18

Hydrogenation of Cyclohexene

A 20-mL Schlenk tube equipped with a magnetic stirrer was heat dried while pumping to a vacuum of 5 Pa before its interior was purged with argon atmosphere. Into the Schlenk tube, iron complex A (25 mg, 0.05 mmol) was admitted as catalyst and dissolved in toluene (2 mL). To the solution, cyclohexene (108 µL, 1.0 mmol) was added. The solution was freeze deaerated, after which the Schlenk tube was purged with hydrogen atmosphere. The solution was stirred at room temperature for 6 hours. With anisole added as internal standard, the geometry and yield of the product were determined by $^1$H-NMR spectroscopy. The resulting compound was identified for geometry by $^1$H and $^{13}$C-NMR spectroscopy. The results are shown as Entry 3 in Table 4.

$^1$H NMR (CDCl$_3$, 395 MHz): δ=1.43 (s, 12H, CH$_2$).
$^{13}$C NMR (CDCl$_3$, 100 MHz): δ=27.0.

Example 19

Hydrogenation of Cyclopentene

A 20-mL Schlenk tube equipped with a magnetic stirrer was heat dried while pumping to a vacuum of 5 Pa before its interior was purged with argon atmosphere. Into the Schlenk tube, iron complex A (25 mg, 0.05 mmol) was admitted as catalyst and dissolved in toluene (2 mL). To the solution, cyclopentene (88.4 µL, 1.0 mmol) was added. The solution was freeze deaerated, after which the Schlenk tube was purged with hydrogen atmosphere. The solution was stirred at room temperature for 6 hours. With anisole added as internal standard, the geometry and yield of the product were determined by $^1$H-NMR spectroscopy. The resulting compound was identified for geometry by $^1$H and $^{13}$C-NMR spectroscopy. The results are shown as Entry 4 in Table 4.

$^1$H NMR (CDCl$_3$, 395 MHz): δ=1.52 (s, 10H, CH$_2$).
$^{13}$C NMR (CDCl$_3$, 100 MHz): δ=25.9.

Example 20

Hydrogenation of 1-methyl-1-cyclohexene

A 20-mL Schlenk tube equipped with a magnetic stirrer was heat dried while pumping to a vacuum of 5 Pa before its interior was purged with argon atmosphere. Into the Schlenk tube, iron complex A (25 mg, 0.05 mmol) was admitted as catalyst and dissolved in toluene (2 mL). To the solution, 1-methyl-1-cyclohexene (108.6 µL, 1.0 mmol) was added. The solution was freeze deaerated, after which the Schlenk tube was purged with hydrogen atmosphere. The solution was stirred at room temperature for 6 hours. With anisole added as internal standard, the geometry and yield of the product were determined by $^1$H-NMR spectroscopy. The resulting compound was identified for geometry by $^1$H and $^{13}$C-NMR spectroscopy. The results are shown as Entry 5 in Table 4.

$^1$H NMR (CDCl$_3$, 395 MHz): δ=0.86 (d, J$_{HH}$=5.8 Hz, 3H, CH$_3$), 1.04-1.28 (m, 4H, CH$_2$), 1.28-1.39 (m, 1H, CH), 1.54-1.72 (m, 6H, CH$_2$).

$^{13}$C NMR (CDCl$_3$, 100 MHz): δ=22.9, 26.3, 26.4, 32.7, 35.4.

Example 21

Hydrogenation of 2,3-dimethyl-2-butene

A 20-mL Schlenk tube equipped with a magnetic stirrer was heat dried while pumping to a vacuum of 5 Pa before its interior was purged with argon atmosphere. Into the Schlenk tube, iron complex A (25 mg, 0.05 mmol) was admitted as catalyst and dissolved in toluene (2 mL). To the solution, 2,3-dimethyl-2-butene (108.9 µL, 1.0 mmol) was added. The solution was freeze deaerated, after which the Schlenk tube was purged with hydrogen atmosphere. The solution was stirred at room temperature for 6 hours. With anisole added as internal standard, the geometry and yield of the product were determined by $^1$H-NMR spectroscopy. The resulting compound was identified for geometry by $^1$H and $^{13}$C-NMR spectroscopy. The results are shown as Entry 6 in Table 4.

$^1$H NMR (CDCl$_3$, 395 MHz): δ=0.84 (d, J$_{HH}$=6.7 Hz, 12H, CH$_3$), 1.40 (septet, J$_{HH}$=6.7 Hz, 2H, CH).

$^{13}$C NMR (CDCl$_3$, 100 MHz): δ=19.4, 33.7.

TABLE 4

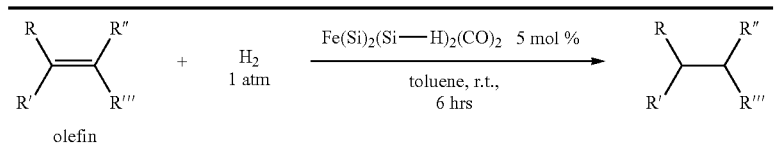

| Entry | Olefin | Yield |
|---|---|---|
| 1 [a] | styrene | 99 |
| 2 | trans-stilbene | 99 (95 [b]) |
| 3 | cyclohexene | 99 |
| 4 | cyclopentene | 99 |

TABLE 4-continued $$\underset{\text{olefin}}{\overset{R}{\underset{R'}{>}}\!\!=\!\!\overset{R''}{\underset{R'''}{<}}} + \underset{1\ \text{atm}}{H_2} \xrightarrow[\text{6 hrs}]{\text{Fe(Si)}_2(\text{Si}\!-\!\!-\!\text{H})_2(\text{CO})_2\ 5\ \text{mol}\%}{\text{toluene, r.t.,}} \underset{R'}{\overset{R}{>}\!\!-\!\!\overset{R''}{<}_{R'''}}$$

| Entry | Olefin | Yield |
|---|---|---|
| 5 | (1-methylcyclohexene) | 59 |
| 6 | (2,3-dimethyl-2-butene) | 20 |

[a] Reaction time is 2 hours.
[b] Isolated yield.

(4) Reductive Reaction of Amide Using Iron Complex A

Example 22

Reduction of N,N-dimethyl-4-methoxybenzamide

A 20-mL eggplant flask equipped with a three-way cock and a magnetic stirrer was heat dried while pumping to a vacuum of 5 Pa before its interior was purged with argon atmosphere. Into the flask, iron complex A (1.0 mg, 0.002 mmol) was admitted as catalyst and dissolved in toluene (0.5 mL). To the solution, 1,2-bis(dimethylsilyl)benzene (475 µL) was added through a syringe, and N,N-dimethyl-4-methoxybenzamide (179 mg, 1.0 mmol) was added. The solution was stirred at 100° C. for 30 minutes. Toluene was distilled off in vacuum. The crude product was purified by silica gel-packed column chromatography using hexane/ethyl acetate (10/1) as developing solvent, obtaining N,N-dimethyl-4-methoxybenzylamine (159 mg, 0.96 mmol, 96%). The results are shown as Entry 1 in Table 5. The resulting amine was identified for geometry by $^1$H and $^{13}$C-NMR spectroscopy and IR spectroscopy.

$^1$H NMR (CDCl$_3$, 395 MHz): δ=2.22 (s, 6H, NMe$_2$), 3.35 (s, 2H, CH$_2$), 3.80 (s, 3H, OMe), 6.85 (d, J=8.7 Hz, 2H, C$_6$H$_4$), 7.21 (d, J=8.7 Hz, 2H, C$_6$H$_4$).

$^{13}$C NMR (CDCl$_3$, 395 MHz): δ=45.22, 55.07, 63.74, 130.23, 113.58, 131.15, 158.71.

IR (neat): ν=1038, 1241, 1510, 2766, 2813, 2941 cm$^{-1}$

Example 23

Reduction of N,N-dimethyl-4-bromobenzamide

A 20-mL eggplant flask equipped with a three-way cock and a magnetic stirrer was heat dried while pumping to a vacuum of 5 Pa before its interior was purged with argon atmosphere. Into the flask, iron complex A (1.0 mg, 0.002 mmol) was admitted as catalyst and dissolved in toluene (0.5 mL). To the solution, 1,2-bis(dimethylsilyl)benzene (475 µL) was added through a syringe, and N,N-dimethyl-4-bromobenzamide (228 mg, 1.0 mmol) was added. The solution was stirred at 100° C. for 30 minutes. Toluene was distilled off in vacuum. The crude product was purified by silica gel-packed column chromatography using hexane/ethyl acetate (20/1) as developing solvent, obtaining N,N-dimethyl-4-bromobenzylamine (184 mg, 0.86 mmol, 86%). The results are shown as Entry 2 in Table 5. The resulting amine was identified for geometry by $^1$H and $^{13}$C-NMR spectroscopy and IR spectroscopy.

$^1$H NMR (CDCl$_3$, 395 MHz): δ=2.22 (s, 6H, NMe$_2$), 3.36 (s, 2H, CH$_2$), 7.18 (d, J×8.70 Hz, 2H, C$_6$H$_4$), 7.44 (d, J=8.70 Hz, 5H, C$_6$H$_4$).

$^{13}$C NMR (CDCl$_3$, 395 MHz): δ=45.97, 64.30, 121.45, 131.33, 131.97, 138.67.

IR (neat): ν=1011, 1487, 2767, 2815, 2941 cm$^{-1}$.

Example 24

Reduction of N,N-dimethyl-4-methoxycarbonylbenzamide

A 20-mL eggplant flask equipped with a three-way cock and a magnetic stirrer was heat dried while pumping to a vacuum of 5 Pa before its interior was purged with argon atmosphere. Into the flask, iron complex A (1.0 mg, 0.002 mmol) was admitted as catalyst and dissolved in toluene (0.5 mL). To the solution, 1,2-bis(dimethylsilyl)benzene (475 µL) was added through a syringe, and N,N-dimethyl-4-methoxycarbonylbenzamide (207 mg, 1.0 mmol) was added. The solution was stirred at 100° C. for 30 minutes. Toluene was distilled off in vacuum. The crude product was purified by silica gel-packed column chromatography using hexane/ethyl acetate (10/1) as developing solvent, obtaining N,N-dimethyl-4-methoxycarbonylbenzylamine (162 mg, 0.84 mmol, 84%). The results are shown as Entry 3 in Table 5. The resulting amine was identified for geometry by $^1$H and $^{13}$C-NMR spectroscopy and IR spectroscopy.

$^1$H NMR (CDCl$_3$, 395 MHz): δ=2.24 (s, 6H, NMe$_2$), 3.47 (s, 2H, CH$_2$), 3.91 (s, 3H, OMe), 7.38 (d, J=7.7 Hz, 2H, C$_6$H$_4$), 7.99 (d, J=7.7 Hz, 2H, C$_6$H$_4$).

$^{13}$C NMR (CDCl$_3$, 395 MHz): δ=45.27, 51.81, 63.84, 128.68, 128.76, 129.40, 144.24, 166.87.

IR (neat): ν=1110, 1275, 2948, 1719, 2768, 2817 cm$^{-1}$

Example 25

Reduction of N,N-dimethyl-3-phenylpropanamide

A 20-mL eggplant flask equipped with a three-way cock and a magnetic stirrer was heat dried while pumping to a vacuum of 5 Pa before its interior was purged with argon atmosphere. Into the flask, iron complex A (1.0 mg, 0.002 mmol) was admitted as catalyst and dissolved in toluene (0.5 mL). To the solution, 1,2-bis(dimethylsilyl)benzene (475 μL) was added through a syringe, and N,N-dimethyl-3-phenyl-propanamide (177 mg, 1.0 mmol) was added. The solution was stirred at 100° C. for 30 minutes. Toluene was distilled off in vacuum. The crude product was purified by silica gel-packed column chromatography using hexane/ethyl acetate (10/1) as developing solvent, obtaining N,N-dimethyl-3-phenylpropylamine (159 mg, 0.83 mmol, 83%). The results are shown as Entry 4 in Table 5. The resulting amine was identified for geometry by $^1$H and $^{13}$C-NMR spectroscopy and IR spectroscopy.

$^1$H NMR (CDCl$_3$, 395 MHz): δ=1.80 (quint, J=7.7 Hz, 2H, CH$_2$), 2.23 (s, 6H, NMe$_2$), 2.30 (t, J=7.7 Hz, 2H, CH$_2$), 2.65 (t, J=7.7 Hz, 2H, CH$_2$), 7.24-7.16 (m, 3H, C$_6$H$_4$), 7.35-7.25 (m, 2H, C$_6$H$_4$).

$^{13}$C NMR (CDCl$_3$, 395 MHz): δ=29.57, 33.79, 45.60, 59.41, 125.84, 128.42, 128.50, 142.40.

IR (neat): ν=1030, 1496, 2764, 2942, 3025, 3060 cm$^{-1}$.

Example 26

Reduction of N-benzyl-ε-caprolactam

A 20-mL eggplant flask equipped with a three-way cock and a magnetic stirrer was heat dried while pumping to a vacuum of 5 Pa before its interior was purged with argon atmosphere. Into the flask, iron complex A (1.0 mg, 0.002 mmol) was admitted as catalyst and dissolved in toluene (0.5 mL). To the solution, 1,2-bis(dimethylsilyl)benzene (475 μL) was added through a syringe, and N-benzyl-ε-caprolactam (203 mg, 1.0 mmol) was added. The solution was stirred at 100° C. for 30 minutes. Toluene was distilled off in vacuum. The crude product was purified by silica gel-packed column chromatography using hexane/ethyl acetate (10/1) as developing solvent, obtaining 1-benzylazepane (169 mg, 0.89 mmol, 89%). The results are shown as Entry 5 in Table 5. The resulting amine was identified for geometry by $^1$H and $^{13}$C-NMR spectroscopy and IR spectroscopy.

$^1$H NMR (CDCl$_3$, 395 MHz): δ=1.58 (br, 8H, CH$_2$), 2.57 (d, J=5.8 Hz, 2H, CH$_2$), 3.60 (s, 2H, PhCH$_2$), 7.22-7.13 (m, 2H, C$_6$H$_4$), 7.33-7.22 (m, 3H, C$_6$H$_4$).

$^{13}$C NMR (CDCl$_3$, 395 MHz): δ=27.19, 28.40, 55.76, 62.90, 126.79, 128.22, 128.90, 140.30.

IR (neat): ν=1071, 1354, 1452, 2851, 2923 cm$^{-1}$.

TABLE 5

| Entry | Reactant | Catalyst concentration (mol %) | Reaction time (hr) | Reaction temperature (° C.) | Product | Yield (%) |
|---|---|---|---|---|---|---|
| 1 | 4-MeO-C$_6$H$_4$-C(O)-N(Me)$_2$ | 0.2 | 0.5 | 100 | 4-MeO-C$_6$H$_4$-CH$_2$-N(Me)$_2$ | 96 |
| 2 | 4-Br-C$_6$H$_4$-C(O)-N(Me)$_2$ | 0.2 | 0.5 | 100 | 4-Br-C$_6$H$_4$-C(O)-N(Me)$_2$ | 86 |
| 3 | 4-(MeO-C(O))-C$_6$H$_4$-C(O)-N(Me)$_2$ | 0.2 | 0.5 | 100 | 4-(MeO-C(O))-C$_6$H$_4$-CH$_2$-N(Me)$_2$ | 84 |
| 4 | Ph-CH$_2$CH$_2$-C(O)-N(Me)$_2$ | 0.2 | 0.5 | 100 | Ph-CH$_2$CH$_2$CH$_2$-N(Me)$_2$ | 83 |
| 5 | N-benzyl-ε-caprolactam | 0.2 | 0.5 | 100 | 1-benzylazepane | 89 |

(5) Reductive Reaction of Aldehyde Using Iron Complex A

Example 27

Reduction of 3-phenylpropionaldehyde

A 30-mL eggplant flask equipped with a magnetic stirrer was heat dried while pumping to a vacuum of 5 Pa before its interior was purged with nitrogen atmosphere. To the flask, ethyl acetate (3/1) as developing solvent, obtaining 4-methoxybenzyl alcohol (131 mg, 0.95 mmol, 95%). The results as are shown as Entry 2 in Table 6. The resulting alcohol was identified for geometry by $^1$H and $^{13}$C-NMR spectroscopy.

$^1$H NMR (CDCl$_3$, 395 MHz): δ=1.74 (br, 1H, OH), 3.81 (s, 3H, CH$_3$O), 4.62 (s, 2H, CH$_2$), 6.89-6.91 (m, 2H, C$_6$H$_4$), 7.26-7.31 (m, 2H, C$_6$H$_4$).

$^{13}$C NMR (CDCl$_3$, 99.5 MHz): δ=55.2, 64.8, 113.9, 128.5, 133.1, 159.1.

TABLE 6

| Entry | Reactant | Catalyst concentration (mol %) | Reaction time (hr) | Reaction temperature (° C.) | Product | Yield (%) |
|---|---|---|---|---|---|---|
| 1 | 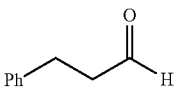 | 1 | 3 | RT | 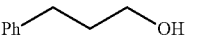 | 88 |
| 2 | 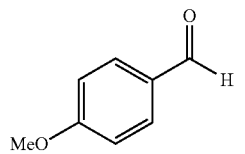 | 1 | 3 | RT | 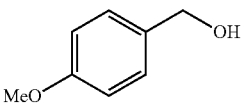 | 95 |

3-phenylpropionaldehyde (136 mg, 1.0 mmol) and 1,1,1,3,3-pentamethyldisiloxane (371 mg, 2.5 mmol) were added through a syringe, and iron complex A (5 mg, 0.01 mmol) was admitted as catalyst. The solution was stirred at room temperature for 3 hours. At 0° C., THF (1 mL) and tetrabutylammonium fluoride in THF (1 M, 1 mL) were then added to the solution, which was stirred at 0° C. for 1 hour. THF was distilled off in vacuum. The crude product was purified by silica gel-packed column chromatography using hexane/ethyl acetate (3/1) as developing solvent, obtaining 3-phenylpropyne-1-ol (120 mg, 0.88 mmol, 88%). The results are shown as Entry 1 in Table 6. The resulting alcohol was identified for geometry by $^1$H and $^{13}$C-NMR spectroscopy.

$^1$H NMR (CDCl$_3$, 395 MHz): δ=1.27 (br, 1H, OH), 1.87-1.94 (m, 2H, CH$_2$CH$_2$CH$_2$), 2.72 (t, J=7.3 Hz, 2H, PhCH$_2$), 3.66-3.71 (m, 2H, CH$_2$OH), 7.17-7.21 (m, 3H, C$_6$H$_5$), 7.27-7.31 (m, 2H, C$_6$H$_5$).

$^{13}$C NMR (CDCl$_3$, 99.5 MHz): δ=32.1, 34.2, 62.3, 125.9, 128.40, 128.42, 141.8.

Example 28

Reduction of 4-methoxybenzaldehyde

A 30-mL eggplant flask equipped with a magnetic stirrer was heat dried while pumping to a vacuum of 5 Pa before its interior was purged with nitrogen atmosphere. To the flask, 4-methoxybenzaldehyde (140 mg, 1.0 mmol) and 1,1,1,3,3-pentamethyldisiloxane (371 mg, 2.5 mmol) were added through a syringe, and iron complex A (5 mg, 0.01 mmol) was admitted as catalyst. The solution was stirred at room temperature for 3 hours. At 0° C., THF (1 mL) and tetrabutylammonium fluoride in THF (1 M, 1 mL) were then added to the solution, which was stirred at 0° C. for 1 hour. THF was distilled off in vacuum. The crude product was purified by silica gel-packed column chromatography using hexane/

(6) Reductive Reaction of Ketone Using Iron Complex A

Example 29

Reduction of 4-methoxyacetophenone

A 30-mL eggplant flask equipped with a magnetic stirrer was heat dried while pumping to a vacuum of 5 Pa before its interior was purged with nitrogen atmosphere. To the flask, 4-methoxyacetophenone (151 mg, 1.0 mmol) and 1,1,1,3,3-pentamethyldisiloxane (372 mg, 2.5 mmol) were added through a syringe, and dissolved in benzene (0.5 mL). To the solution, iron complex A (5.0 mg, 0.01 mmol) was added as catalyst. The solution was stirred at room temperature for 6 hours. At 0° C., tetrabutylammonium fluoride in THF (1 M, 1 mL) was then added to the solution, which was stirred at 0° C. for 1 hour. The solvents were distilled off in vacuum. The crude product was purified by silica gel-packed column chromatography using hexane/ethyl acetate (3/1) as developing solvent, obtaining 1-(4-methoxyphenyl)ethanol (140 mg, 0.92 mmol, 92%). The results are shown as Entry 1 in Table 7. The resulting alcohol was identified for geometry by $^1$H and $^{13}$C-NMR spectroscopy.

$^1$H NMR (CDCl$_3$, 395 MHz): δ=1.49 (d, J=6.8 Hz, 3H, CH$_3$), 1.70 (br, 1H, OH), 3.81 (s, 3H, CHO), 4.87 (q, J=6.3 Hz, 1H, CC), 6.87-6.90 (m, 2H, C$_6$H$_4$), 7.29-7.32 (m, 2H, C$_6$H$_4$).

$^{13}$C NMR (CDCl$_3$, 99.5 MHz): δ=25.0, 55.3, 70.0, 113.9, 126.6, 138.0, 159.0.

Example 30

Reduction of 4-phenyl-2-butanone

A 30-mL eggplant flask equipped with a magnetic stirrer was heat dried while pumping to a vacuum of 5 Pa before its interior was purged with nitrogen atmosphere. To the flask, 4-phenyl-2-butanone (148 mg, 1.0 mol) and 1,1,1,3,3-pentamethyldisiloxane (371 mg, 2.5 mmol) were added through a syringe, and iron complex A (5.0 mg, 0.01 mmol) was added as catalyst. The solution was stirred at room temperature for 24 hours. At 0° C., THF (1 mL) and tetrabutylammonium fluoride in THF (1 M, 1 mL) were then added to the solution, which was stirred at 0° C. for 1 hour. The solvent was distilled off in vacuum. The crude product was purified by silica gel-packed column chromatography using hexane/ethyl acetate (3/1) as developing solvent, obtaining 4-phenyl-1-butanol (139 mg, 0.92 mmol, 92%). The results are shown as Entry 2 in Table 7. The resulting alcohol was identified for geometry by $^1$H and $^{13}$C-NMR spectroscopy.

$^1$H NMR (CDCl$_3$, 395 MHz): δ=1.23 (d, J=6.3 Hz, 3H, CH$_3$), 1.32 (br, 1H, OH), 1.75-1.81 (m, 2H, CH$_2$CH$_2$CH), 2.64-2.75 (m, 2H, PhCH$_2$), 3.83 (m, 1H, CH).

$^{13}$C NMR (CDCl$_3$, 99.5 MHz): δ=23.4, 32.0, 40.7, 67.2, 125.7, 128.25, 128.27, 142.0.

shown as Entry 1 in Table 8. The resulting alcohol was identified for geometry by $^1$H and $^{13}$C-NMR spectroscopy.

$^1$H NMR (CDCl$_3$, 395 MHz): δ=1.27 (br, 1H, OH), 1.87-1.94 (m, 2H, CH$_2$CH$_2$CH$_2$), 2.72 (t, J=7.3 Hz, 2H, PhCH$_2$), 3.66-3.71 (m, 2H, CH$_2$OH), 7.17-7.21 (m, 3H, C$_6$H$_5$), 7.27-7.31 (m, 2H, C$_6$H$_5$).

$^{13}$C NMR (CDCl$_3$, 99.5 MHz): δ=32.1, 34.2, 62.3, 125.9, 128.40, 128.42, 141.8.

Example 32

Reduction of Isopropyl Cyclohexanecarboxylate

A 30-mL eggplant flask equipped with a magnetic stirrer was heat dried while pumping to a vacuum of 5 Pa before its interior was purged with nitrogen atmosphere. To the flask, isopropyl cyclohexanecarboxylate (171 mg, 1.0 mmol) and

TABLE 7

| Entry | Reactant | Catalyst concentration (mol %) | Reaction time (hr) | Reaction temperature (° C.) | Product | Yield (%) |
|---|---|---|---|---|---|---|
| 1 | 4'-methoxyacetophenone | 1 | 6 | RT | 1-(4-methoxyphenyl)ethanol | 92 |
| 2 | 4-phenyl-2-butanone | 1 | 24 | 100 | 4-phenyl-2-butanol | 92 |

(7) Reductive Reaction of Eater Using Iron Complex A

Example 31

Reduction of methyl 3-phenylpropionate

A 30-mL eggplant flask equipped with a magnetic stirrer was heat dried while pumping to a vacuum of 5 Pa before its interior was purged with nitrogen atmosphere. To the flask, methyl 3-phenylpropionate (167 mg, 1.0 mmol) and 1,1,3,3-tetramethyldisiloxane (336 mg, 2.5 mmol) were added through a syringe, and iron complex A (15 mg, 0.03 mol) was added as catalyst. The solution was stirred at room temperature for 3 hours. At 0° C., THF (1 mL) and tetrabutylammonium fluoride in THF (1 M, 1 mL) were then added to the solution, which was stirred at 0° C. for 1 hour. THF was distilled off in vacuum. The crude product was purified by silica gel-packed column chromatography using hexane/ethyl acetate (5/1) as developing solvent, obtaining 3-phenylpropan-1-ol (131 mg, 0.96 mmol, 96%). The results are 1,1,3,3-tetramethyldisiloxane (335 mg, 2.5 mmol) were added through a syringe, and iron complex A (15 mg, 0.03 mmol) was added as catalyst. The solution was stirred at room temperature for 3 hours. At 0° C., THF (1 mL) and tetrabutylammonium fluoride in THF (1 M, 1 mL) were then added to the solution, which was stirred at 0° C. for 1 hour. THF was distilled off in vacuum. The crude product was purified by silica gel-packed column chromatography using hexane/ethyl acetate (3/1) as developing solvent, obtaining cyclohexane methanol (83 mg, 0.73 mmol, 73%). The results are shown as Entry 2 in Table 8. The resulting alcohol was identified for geometry by $^1$H and $^{13}$C-NMR spectroscopy.

$^1$H NMR (CDCl$_3$, 395 MHz): δ=0.89-0.99 (m, 2H), 1.11-1.32 (m, 4H), 1.43-1.54 (m, 1H), 1.55 (br, 1H, OH), 1.66-1.78 (m, 4H), 3.44 (t, J=5.32, 2H, CH$_2$OH).

$^{13}$C NMR (CDCl$_3$, 99.5 MHz): δ=25.8, 26.6, 29.6, 40.5, 68.8.

TABLE 8

| Entry | Reactant | Catalyst concentration (mol %) | Reaction time (hr) | Reaction temperature (° C.) | Product | Yield (%) |
|---|---|---|---|---|---|---|
| 1 | methyl 3-phenylpropionate | 3 | 3 | RT | 3-phenylpropan-1-ol | 96 |

TABLE 8-continued

| Entry | Reactant | Catalyst concentration (mol %) | Reaction time (hr) | Reaction temperature (° C.) | Product | Yield (%) |
|---|---|---|---|---|---|---|
| 2 | cyclohexyl-C(=O)-Oi-Pr | 3 | 3 | RT | cyclohexyl-CH₂-OH | 73 |

(8) Hydrosilylation Reaction Using Iron Complex B

Example 33

Hydrosilylation of ethylene with 1,1,1,3,3-pentamethyldisiloxane

A 20-mL Schlenk tube equipped with a magnetic stirrer was heat dried while pumping to a vacuum of 5 Pa before its interior was purged with argon atmosphere. Into the Schlenk tube, iron complex B (13 mg, 0.03 mol) was admitted as catalyst. To the tube, 1,1,1,3,3-pentamethyldisiloxane (195.2 µL, 1.0 mmol) was added. The solution was freeze deaerated, after which the Schlenk tube was purged with ethylene atmosphere. The solution was stirred at 80° C. for 16 hours. After cooling, anisole was added as internal standard. By $^1$H-NMR spectroscopy, the geometry and yield of the product were determined (yield 38%). The resulting compound was identified for geometry by $^1$H, $^{13}$C and $^{29}$Si-NMR spectroscopy.

$^1$H NMR (600 MHz, CDCl$_3$): δ=0.03 (s, 6H, Si(CH$_3$)$_2$), 0.06 (s, 9H, Si(CH$_3$)$_2$), 0.49 (q, J$_{HH}$=8.2 Hz, 2H, SiCH$_2$CH$_3$), 0.92 (t, J$_{HH}$=8.2 Hz, 3H, CH$_2$CH$_3$).

$^{13}$C NMR (100 MHz, CDCl$_3$): δ=−0.28, 1.93, 6.72, 10.03.

$^{29}$Si NMR (119 MHz, CDCl$_3$): δ=7.05, 8.60.

(9) Hydrogenation Reaction Using Iron Complex B

Example 34

Hydrogenation of Styrene

A 20-mL Schlenk tube equipped with a magnetic stirrer was heat dried while pumping to a vacuum of 5 Pa before its interior was purged with argon atmosphere. Into the Schlenk tube, iron complex B (11 mg, 0.025 mol) was admitted as catalyst and dissolved in toluene (2 mL). To the solution, styrene (57 µL, 0.5 mmol) was added. The solution was freeze deaerated, after which the Schlenk tube was purged with hydrogen atmosphere. The solution was stirred at 100° C. for 16 hours. With anisole (108.6 µL, 1.0 mmol) added as internal standard, the geometry and yield of the product were determined by $^1$H-NMR spectroscopy (yield 35%). The resulting compound was identified for geometry by $^1$H and $^{13}$C-NMR spectroscopy.

$^1$H NMR (CDCl$_3$, 395 MHz): δ=1.13 (t, J$_{HH}$=7.2 Hz, 3H, CH$_2$CH$_3$), 2.54 (q, J$_{HH}$=7.2 Hz, 2H, CH$_2$CH$_3$), 7.02-7.11 (m, 3H, C$_6$H$_5$), 7.11-7.20 (m, 2H, C$_6$H$_5$).

$^{13}$C NMR (100 MHz, CDCl$_3$): δ=15.6, 28.8, 125.6, 127.8, 128.3, 144.3.

(10) Reductive Reaction of Amide Using Iron Complex B

Example 351

Reduction of N,N-dimethyl-4-methoxybenzamide

A 20-mL eggplant flask equipped with a three-way cock and a magnetic stirrer was heat dried while pumping to a vacuum of 5 Pa before its interior was purged with argon atmosphere. Into the flask, iron complex B (11 mg, 0.025 mmol) was admitted as catalyst and dissolved in toluene (0.25 mL). To the solution, 1,2-bis(dimethylsilyl)benzene (238 µL) was added through a syringe, and N,N-dimethyl-4-methoxybenzamide (90 mg, 0.5 mmol) was added. The solution was stirred at 100° C. for 16 hours. After cooling, with ferrocene (18.6 mg, 1.0 mmol) added as internal standard, the geometry and yield of the product were determined by $^1$H-NMR spectroscopy (yield 99%). The resulting compound was identified for geometry by $^1$H and $^{13}$C-NMR spectroscopy and IR spectroscopy.

$^1$H NMR (CDCl$_3$, 395 MHz): δ=2.22 (s, 6H, NMe$_2$), 3.35 (e, 2H, CH$_2$), 3.80 (s, 3H, OMe), 6.85 (d, J=8.7 Hz, 2H, C$_6$H$_4$), 7.21 (d, J=8.7 Hz, 2H, C$_6$H$_4$).

$^{13}$C NMR (CDCl$_3$, 395 MHz): δ=45.22, 55.07, 63.74, 130.23, 113.58, 131.15, 158.71.

IR (neat): ν=1038, 1241, 1510, 2766, 2813, 2941 cm$^{-1}$

The invention claimed is:

1. A mononuclear iron complex having formula (1):

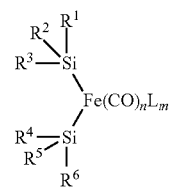

(1)

wherein
R$^1$ to R$^6$ are each independently hydrogen, or an alkyl, aryl, aralkyl, organoxy, monoorganoamino, diorganoamino, monoorganophosphino, diorganophosphino, monoorganosilyl, diorganosilyl, triorganosilyl, or organothio group which may be substituted with X, or at least one pair of any one of R$^1$ to R$^3$ and any one of R$^4$ to R$^6$, taken together, represent a crosslinking substituent, and X is a halogen atom, organoxy, monoorganoamino, diorganoamino or organothio group, L is at least one two-electron ligand selected from the group consisting of molecular hydrogen, amines, amines, nitrogen-containing heterocycles, arsines, alcohols, thiols, ethers, sulfides, nitriles, isonitriles, aldehydes, ketones, alkenes, alkynes, and hydrosilanes, with the proviso that when a plurality of L's are present, they may be the same or different, and when two L's are present, they may bond together, and n and m are each independently an integer of 1 to 3, provided that n+m is 3 or 4.

2. The mononuclear iron complex of claim 1 wherein L is at least one two-electron ligand selected from the group consisting of molecular hydrogen, amine, imine, nitrogen-containing heterocycle, arsine, alcohol, thiol, ether, sulfide, nitrile, isonitrile, aldehyde, ketone, $C_2$-$C_{30}$ alkene, $C_2$-$C_{30}$ alkyne, and triorganohydrosilane.

3. The mononuclear iron complex of claim 1 or 2 wherein n and m each are 2, and L is at least one ligand selected from sulfide, thiol, and triorganohydrosilane, with the proviso that two L's may bond together.

4. The mononuclear iron complex of claim 3 wherein
$R^1$ to $R^6$ are each independently an alkyl, aryl or aralkyl group which may be substituted with X which is as defined above,
L's are triorganohydrosilanes represented by H—$SiR^7R^8R^9$ and H—$SiR^{10}R^{11}R^{12}$ wherein $R^7$ to $R^{12}$ are each independently an alkyl, aryl or aralkyl group which may be substituted with X which is as defined above,
at least one pair of any one of $R^1$ to $R^3$ and any one of $R^4$ to $R^6$ or any one of $R^7$ to $R^9$, or at least one pair of any one of $R^{10}$ to $R^{12}$ and any one of $R^4$ to $R^6$ or any one of $R^7$ to $R^9$ may bond together to form a crosslinking substituent, or
at least one pair of any one of $R^1$ to $R^3$ and any one of $R^4$ to $R^6$ or any one of $R^7$ to $R^9$ may bond together to form a crosslinking substituent, and at least one pair of any one of $R^{10}$ to $R^{12}$ and any one of $R^4$ to $R^6$ or any one of $R^7$ to $R^9$ may bond together to form a crosslinking substituent.

5. The mononuclear iron complex of claim 3 wherein
$R^1$ to $R^6$ are each independently an alkyl, aryl or aralkyl group which may be substituted with X which is as defined above,
L's are sulfides or thiols represented by $SR^{13}R^{14}$ and $SR^{15}R^{16}$ wherein $R^{13}$ to $R^{16}$ are each independently hydrogen or an alkyl, aryl or aralkyl group which may be substituted with X which is as defined above,
at least one pair of either one of $R^{13}$ and $R^{14}$ and either one of $R^{15}$ and $R^{16}$ may bond together to form a crosslinking substituent.

6. The mononuclear iron complex of claim 1 wherein a pair of any one of $R^1$ to $R^3$ and any one of $R^4$ to $R^6$ bond together to form a crosslinking substituent.

7. The mononuclear iron complex of claim 4 wherein any one of $R^1$ to $R^3$ and any one of $R^4$ to $R^6$ or any one of $R^7$ to $R^9$ bond together to form a crosslinking substituent, and any one of $R^{10}$ to $R^{12}$ and a substituent on Si which is selected from any one of $R^4$ to $R^6$ and any one of $R^7$ to $R^9$ and which does not participate in formation of said crosslinking substituent, bond together to form a crosslinking substituent.

8. The mononuclear iron complex of claim 5 wherein either one of $R^{13}$ and $R^{14}$ and either one of $R^{15}$ and $R^{16}$ bond together to form a crosslinking substituent.

9. The mononuclear iron complex of claim 7 wherein any one of $R^1$ to $R^3$ and any one of $R^4$ to $R^6$ bond together to form an o-phenylene group which may be substituted with Y, Y is hydrogen, halogen, $C_1$-$C_{10}$ alkyl, or $C_1$-$C_{10}$ alkoxy group, with the proviso that when a plurality of Y's are present, they may be the same or different, and any one of $R^{10}$ to $R^{12}$ and any one of $R^7$ to $R^9$ bond together to form an o-phenylene group which may be substituted with Y which is as defined above.

10. The mononuclear iron complex of claim 8 wherein any one of $R^1$ to $R^3$ and any one of $R^4$ to $R^6$ bond together to form an o-phenylene group which may be substituted with Y, Y is hydrogen, halogen, $C_1$-$C_{10}$ alkyl, or $C_1$-$C_{10}$ alkoxy group, with the proviso that when a plurality of Y's are present, they may be the same or different, and either one of $R^{13}$ and $R^{14}$ and either one of $R^{15}$ and $R^{16}$ bond together to form a $C_1$-$C_6$ alkylene group.

11. A catalyst comprising a mononuclear iron complex having formula (1):

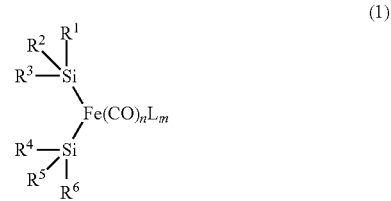

wherein
$R^1$ to $R^6$ are each independently hydrogen, or an alkyl, aryl, aralkyl, organoxy, monoorganoamino, diorganoamino, monoorganophosphino, diorganophosphino, monoorganosilyl, diorganosilyl, triorganosilyl, or organothio group which may be substituted with X, or at least one pair of any one of $R^1$ to $R^3$ and any one of $R^4$ to $R^6$, taken together, represent a crosslinking substituent, and X is a halogen atom, organoxy, monoorganoamino, diorganoamino or organothio group,
L is a two-electron ligand other than CO, with the proviso that when a plurality of L's are present, they may be the same or different, and when two L's are present, they may bond together, and
n and m are each independently an integer of 1 to 3, provided that n+m is 3 or 4, the catalyst having activity to three reactions: hydrosilylation reaction, hydrogenation reaction, and reductive reaction of carbonyl compounds.

12. A method for preparing an addition compound, comprising the step of effecting hydrosilylation reaction of a compound having an aliphatic unsaturated bond with a hydrosilane or organohydropolysiloxane having a Si—H bond in the presence of the catalyst of claim 11.

13. A method for preparing an alkane compound, comprising the step of hydrogenating a compound having an aliphatic unsaturated bond in the presence of the catalyst of claim 11.

14. A method for preparing an amine compound, comprising the step of reducing an amide compound with a silane or organohydropolysiloxane having a Si—H bond in the presence of the catalyst of claim 11.

15. A method for preparing an alcohol compound, comprising the step of reducing an aldehyde, ketone or ester compound with a silane or organohydropolysiloxane having a Si—H bond in the presence of the catalyst of claim 11.

* * * * *